(12) United States Patent
Kim

(10) Patent No.: US 8,753,694 B2
(45) Date of Patent: Jun. 17, 2014

(54) ANTI-ANGIOGENIC AGENTS AND ANTI-OBESITY SUBSTANCES APPLIED WITH ANTI-ANGIOGENESIS FROM NATURAL PRODUCTS

(75) Inventor: Jong-Deog Kim, Yeosu-si (KR)

(73) Assignee: Industry Foundation of Chonnam National University, Gwangju (KR)

( * ) Notice: Subject to any disclaimer, the term of this patent is extended or adjusted under 35 U.S.C. 154(b) by 333 days.

(21) Appl. No.: 12/731,887

(22) Filed: Mar. 25, 2010

(65) Prior Publication Data

US 2010/0247691 A1    Sep. 30, 2010

(30) Foreign Application Priority Data

Mar. 31, 2009  (KR) .................. 10-2009-0027470

(51) Int. Cl.
*A61K 36/00*    (2006.01)

(52) U.S. Cl.
USPC ......................................................... 424/725

(58) Field of Classification Search
USPC ......................................................... 424/725
See application file for complete search history.

(56) References Cited

U.S. PATENT DOCUMENTS

| 6,436,448 | B1 * | 8/2002 | Yue ................................. 424/725 |
| 2007/0031332 | A1 | 2/2007 | Greenway et al. |

FOREIGN PATENT DOCUMENTS

| KR | 1019990084077 | | 12/1999 |
| KR | 1020030075067 | | 9/2003 |
| KR | 2004003923 | A * | 1/2004 |
| KR | 2004060098 | A * | 7/2004 |
| KR | 1020040062832 | | 7/2004 |
| KR | 1020050111658 | | 11/2005 |
| KR | 1020100109073 | | 10/2010 |

OTHER PUBLICATIONS

Bhattacharyya et al. Synthesis of Acetic Acid From Methanol and Carbon Monoxide in the Vapour Phase in Presence of Nickel Catalysts at High Pressures; J. appl. Chem, 6, Oct. 1956, pp. 442-456.*
Kim et al. PTP1B inhibitory activity of kaurane diterpenes isolated from *Siegesbeckia glabrescens*; Journal of enzyme inhibition and medicinal chemistry, (Aug. 2006) vol. 21, No. 4, pp. 379-383, Medline Abstract provided only, 2 pages.*
Sohee et al. PTP1B Inhibitory Activity of Kaurane Diterpenes Isolated From *Siegesbeckia glabrescens*; Journal of Enzyme Inhibition and Medicinal Chemistry (Aug. 2006), vol. 21, No. 4, pp. 379-383.*
Shim, "Protosome Inhibition Activity of Psoraleae Semen and Processed Psoraleae Semen," *Kor. J. Pharmacogn.*, 39(1):56-59 (2008) (English Abstract included with Korean publication).
Leung et al. "Vascular Endothelial Growth Factor is a Secreted Angiogenic Mitogen," *Science*, vol. 246:1306-1309 (1989).

(Continued)

*Primary Examiner* — Patricia Leith
(74) *Attorney, Agent, or Firm* — Klarquist Sparkman, LLP

(57) ABSTRACT

Disclosed herein are an anti-obesity agent from natural products based on angiogenesis inhibitory actions, and an angiogenesis inhibitor or a composition for inhibiting obesity, containing at least one selected from the group consisting of *Psoraleae* Semen extract, *Siegesbeckiae* Herba extract, and Corni Fructus extract. Because the *Psoraleae* Semen extract, *Siegesbeckiae* Herba extract, and Corni Fructus extract of the present invention exhibit angiogenesis inhibitory effects and obesity inhibitory effects, they may be usefully used as an agent for prevention and treatment of angiogenesis-related diseases or obesity.

12 Claims, 17 Drawing Sheets
(17 of 17 Drawing Sheet(s) Filed in Color)

(56) References Cited

OTHER PUBLICATIONS

Hanahan et al. "Patterns and Emerging Mechanisms of the Angiogenic Switch during Tumorigenesis," *Cell*, vol. 86:353-364 (1996).

O'Brien et al. "Neovascular Expression of E-Selectin, Intercellular Adhesion Molecule-1, and Vascular Cell Adhesion Molecule-1 in Human Atherosclerosis and Their Relation to Intimal Leukocyte Content," *American Heart Association*, vol. 93:672-682 (1996).

Adamis et al. "Angiogenesis and ophthalmic disease," *Angiogenesis*, vol. 3:9-14 (1999).

Plate "Mechanisms of Angiogenesis in the Brain," *J. Neuropathol. Exp. Neurol.*, vol. 58(4):313-320 (1999).

Dempsey et al., "Attenuation of Brain Edema, Blood-Brain Barrier Breakdown, and Injury Volume By Ifenprodil, a Polyamine-Site N-Methyl-d-aspartate Receptor Antagonist, after Experimental Traumatic Brain Injury in Rats," *Neurosurgery*. vol. 47(2):399-404; discussion 404-406 (2000).

Gashe et al. "Matrix Metalloproteinase Inhibition Prevents Oxidative Stress-Associated Blood-Brain Barrier Disruption After Transient Focal Cerebral Ischemia," *J. Cere. Blood Flow Metab.*, vol. 21(12):1393-1400 (2001).

Rosenberg "Matrix Metalloproteinases and Neuroinflammation in Multiple Sclerosis," *Neuroscientist*, vol. 8(6):586-595 (2002).

Banks et al. "Passage of amyloid β protein antibody across the blood-brain barrier in a mouse model of Alzheimer's disease," *Peptides*, vol. 23:2223-2226 (2002).

Kucuk et al. "Effects of losartan on the blood-brain barrier permeability in long-term nitric oxide blockade-induced hypertensive rats," *Life Sciences*, vol. 71(8):937-946 (2002).

Rupnick et al. "Adipose tissue mass can be regulated through the vasculature," *PNAS*, vol. 99(16):10730-10735 (2002).

Proescholdt et al. "Vascular Endothelial Growth Factor is Expressed in Multiple Sclerosis Plaques and Can Induce Inflammatory Lesions in Experimental Allergic Encephalomyelitis Rats," *J. Neuropathol. Exp. Neurol.*, vol. 61(10):914-925 (2002).

Esen et al. "Effects of Magnesium Administration on Brain Edema and Blood-Brain Barrier Breakdown After Experimental Traumatic Brain Injury in Rats," *J. Neurosurg. Anesthesiol.*, vol. 15(2):119-125 (2003).

Neels et al. "Angiogenesis in an in vivo model of adipose tissue development," *The FASEB Journal*, 10.1096/fj.03-1101fje. (2004).

Hausman et al. "Adipose tissue angiogenesis," *J. Anim. Sci.*, vol. 82: 925-934 (2004).

Nishimura et al. "Adipogenesis in Obesity Requires Close Interplay Between Differentiating Adipocytes, Stromal Cells, and Blood Vessels," *Diabetes*, vol. 56:1517-1526 (2007).

Liu et al. "Angiogenesis Inhibitors May Regulate Adiposity," *Nutrition Review*, vol. 61(11): 384-387 (2003).

Choi et al., "The Effects of *Chekamuiyiin-tang* on Biochemical and Histological Changes of Rats Fed High Diet," *J. Korean Oriental Med.*, 21(3):31-39, 2000.

Kim et al., Oriental Medicines Effects on Cure and Prevention of an Obesity (VII), *Korean J. Oriental Physiology & Pathology* 16(5):1001-1008, 2002.

Moon et al., "Human and Animal Study on the Natural Food for Obesity and Metabolic Syndrome Risk Factors," *J. Korean Soc. Food Sci. Nutr.*, 32(8), 1394-1400, 2003.

Neff et al., "Pathological effects of pine needle ingestion in pregnant mice," *Cornell Vet.*, downloaded from http://www.ncbi.nlm.nih.gov/pubmed/7083861, 1 pg., 1982.

Park et al., "Effects of Intaking of Red Ginseng Products on Correlationship beween Obesity and Blood Lipids," *Korean J. Biomed. Lab. Sci.*, vol. 6, No. 4, pp. 253-260, Dec. 2000.

Song, "Clinical Trial of Herbal formula (Slim-diet) on Weight Loss in Obese Pre-menopausal Korean Females," *Journal of Korean Oriental Association for Study of Obesity*, 3(1):1-6, 2003.

Swan, "Garlic and chilli—diet foods?", *Health Minutes*, downloaded from http://www.abc.net.au/health/minutes/stories/s349786.htm , 1 pg., Aug. 20, 2001.

Yuan, "Ginseng berry extract shows promise for diabetes, obesity," *The University of Chicago Medicine*, downloaded from http://www.uchospitals.edu/news/2002/20020524-ginseng.html , 3 pp., Mar. 6, 2013.

\* cited by examiner a)

b)

c)

Anti-Akt

Anti-β-actin

| VEGF | - | + | + | + | + | |
| Corni Fructus | - | - | 0.1 | 0.5 | 1 | (ppm) |

ANTI-ANGIOGENIC AGENTS AND ANTI-OBESITY SUBSTANCES APPLIED WITH ANTI-ANGIOGENESIS FROM NATURAL PRODUCTS

CROSS-REFERENCES TO RELATED APPLICATION

This patent application claims the benefit of priority from Korean Patent Application No. 10-2009-0027470, filed on Mar. 31, 2009, the contents of which are incorporated herein by reference.

BACKGROUND OF THE INVENTION

1. Field of the Invention

The present disclosure relates to an anti-obesity substance applied with anti-angiogenesis from natural products.

2. Description of the Related Art

The term "angiogenesis" refers to a series of processes involving the generation of new blood vessels from pre-existing blood vessels, and is known to be essentially required in normal anatomical functions such as fetal development, female menstruation, wound healing, etc.; and various diseases such as growth of cancer and mast cells, rheumatoid arthritis, diabetic blindness, etc. However, it is a very rigorously controlled phenomenon that rarely occurs under normal conditions. In an organism, angiogenesis inducing factors maintain an equilibrium state with angiogenesis inhibiting factors under normal conditions. However, because the number of vascular growth promoting factors increases or vascular growth inhibiting factors do not function properly under disease-causing circumstances, angiogenesis may not be autonomously regulated and may continue to grow, leading to development of disease.

The formation of angiogenesis has been known to be promoted by 20 or more vascular formation promoting factors until now, and vascular endothelial growth factor (VEGF) among them is secreted in various kinds of tumor and mast cells and is known to be the most potent vascular formation promoting factor. The VEGF is also known as a vascular permeability factor and known to bind to the receptors thereof, VEGFR-1 (Flt-1) and VEGFR-2 (Flk-1/KDR), to cause the proliferation of vascular endothelial cells and increase vascular permeability to be involved in the growth and metastasis of tumor and mast cells (Leung D W et al., Science 246: 1306-1309, 1989; Liping Liu & Meydani Mohsen *Nutrition Review,* 61(11): 384-387, 2003; Jaap G et al., *The FASEB Journal* 10.1096/fj.03-1101fje. 2004; Hausman G J & Tichardson R L, *J. anim. Sci.,* 82: 925-934, 2004).

In particular, angiogenesis plays an important role in formation of mast cells and rapidly supplies oxygen and nutrients to obesity tissues to directly aid in the growth of obesity tissues. Therefore, the formation of a new blood vessel in any tissue is inhibited by inhibiting the formation of the new blood vessel to prevent the tissue from hypertrophy. Folkman (PNAS 99: 10730-10735, 2002) reported that a mouse lost weight when an angiogenesis inhibitor was administered, and Nishimura et al., reported that the formation of a new blood vessel directly promoted the growth of mast cells.

Obesity may be defined as a state in which body fat is excessively accumulated to harm the health, and is established as a recognized 'chronic disease' which must be treated because it was revealed that it is responsible for social and psychological disorder as well as increases to mortality and morbidity due to various chronic degenerative diseases such as hypertension, arteriosclerosis, coronary heart disease, type 2 diabetes mellitus, fatty liver, hyperlipidemia, degenerative arthritis, some cancer diseases, etc. Current obesity drugs may include fenfluramine and sibutamine preparations that are suppressors of appetite, which reduce food uptake, and ephedrine and orlistat preparations that inhibit lipogenesis or increase metabolic activity. However, these drugs cause many side effects (alopecia) and addiction problems emerge. Therefore, there is need for development of an anti-obesity agent from natural products.

Thus, the present inventors have discovered *Psoraleae* Semen extract, *Siegesbeckiae* Herba extract, and Corni Fructus extract, which exhibit inhibiting effects of angiogenesis among various extracts from natural products, found that these exhibit anti-obesity effects, confirmed that *Psoraleae* Semen extract, *Siegesbeckiae* Herba extract, and Corni Fructus extract of the present invention may be used as active ingredients for an angiogenesis inhibitor or anti-obesity composition, thereby leading to completion of the present invention.

SUMMARY OF THE INVENTION

One object of the present invention is to provide an angiogenesis inhibitor, a composition for prevention or treatment of angiogenesis-related diseases, or a composition for anti-obesity with the inhibitory activity of angiogenesis, containing *Psoraleae* Semen extract, *Siegesbeckiae* Herba extract, and Corni Fructus extract as active ingredients.

Another object of the present invention is to provide a method for inhibiting angiogenesis, a method for preventing or treating angiogenesis-related diseases, or a method for inhibiting obesity, including administering to an individual an effective amount of *Psoraleae* Semen extract, *Siegesbeckiae* Herba extract, and Corni Fructus extract.

In order to achieve the objects, the present invention provides an angiogenesis inhibitor containing at least one selected from the group consisting of *Psoraleae* Semen extract, *Siegesbeckiae* Herba extract, and Corni Fructus extract as active ingredients.

The present invention also provides a method for inhibiting angiogenesis, including administering to an individual at least one selected from the group consisting of *Psoraleae* Semen extract, *Siegesbeckiae* Herba extract, and Corni Fructus extract.

Furthermore, the present invention provides a composition for prevention or treatment of angiogenesis-related diseases, containing at least one selected from the group consisting of *Psoraleae* Semen extract, *Siegesbeckiae* Herba extract, and Corni Fructus extract as an active ingredient.

The present invention also provides a method for preventing or treating angiogenesis-related diseases, including administering to an individual at least one selected from the group consisting of *Psoraleae* Semen extract, *Siegesbeckiae* Herba extract, and Corni Fructus extract.

Furthermore, the present invention provides a composition for anti-obesity with the inhibitory activity of angiogenesis, containing *Psoraleae* Semen extract or *Siegesbeckiae* Herba extract as active ingredients.

The present invention also provides a method for inhibiting obesity, including administering to an individual an effective amount of *Psoraleae* Semen extract or *Siegesbeckiae* Herba extract.

Furthermore, the present invention provides a health supplement food for preventing or improving antiogenesis-related diseases such as cerebrovascular diseases, cardiovascular diseases, ocular diseases or cancerous diseases, containing at least one selected from the group consisting of Psoraleae Semen extract, Siegesbeckiae Herba extract, and Corni Fructus extract as an active ingredient.

In addition, the present invention provides a health supplement food for preventing or improving obesity, containing Psoraleae Semen extract or Siegesbeckiae Herba extract as an active ingredient.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other objects, features and other advantages of the present invention will be more clearly understood from the following detailed description taken in conjunction with the accompanying drawings, in which:

FIG. 6: Psoraleae Semen;
FIG. 7: Siegesbeckiae Herba; and
FIG. 8: Corni Fructus.

FIG. 11: Psoraleae Semen;
FIG. 12: Siegesbeckiae Herba; and
FIG. 13: Corni Fructus.

DESCRIPTION OF THE PREFERRED EMBODIMENTS

Figure 1:
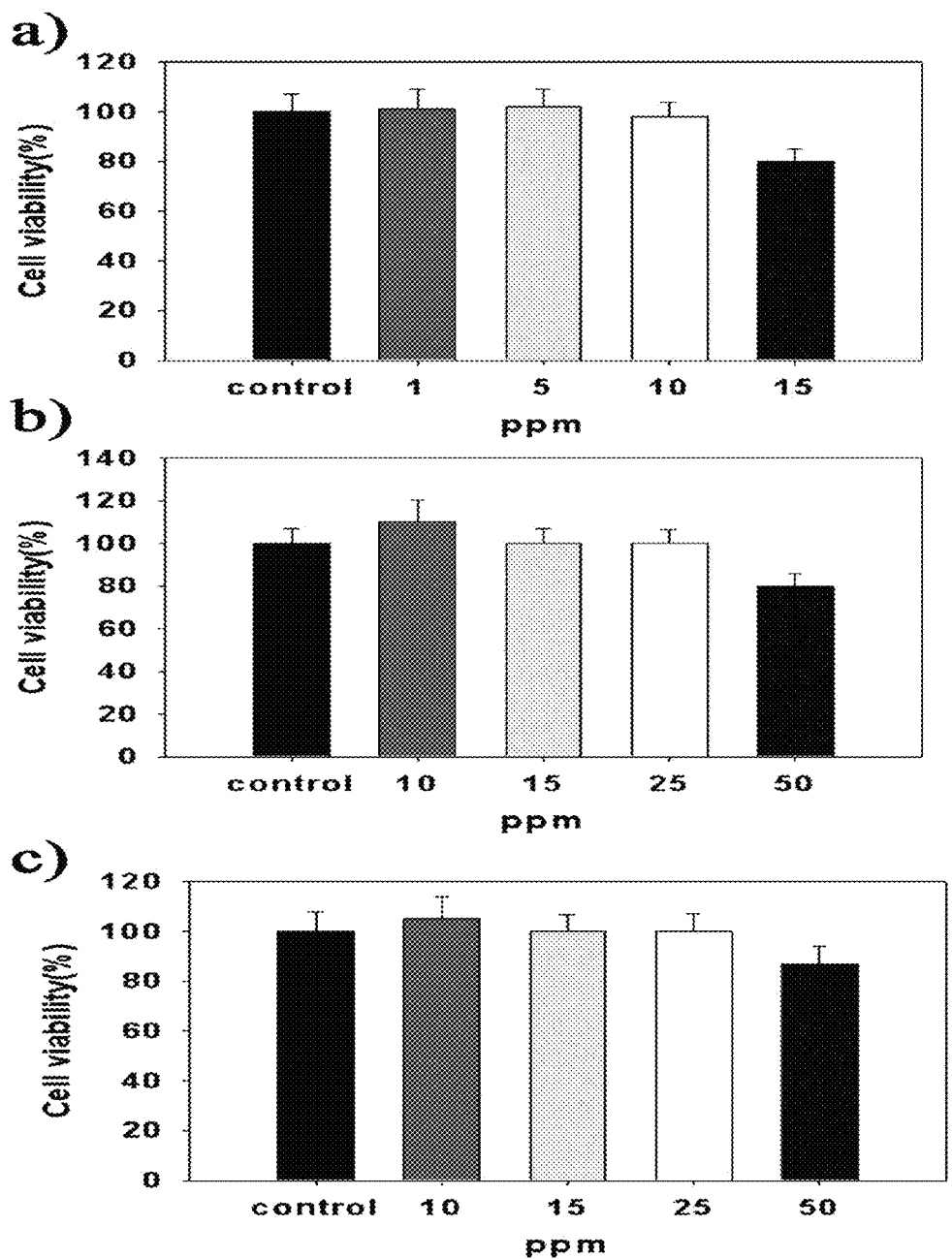
FIG. 1 is a group of graphs confirming the cytotoxicity of each extract of Psoraleae Semen, Siegesbeckiae Herba, and Corni Fructus.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, terms as used herein will be defined.

The term "prevention" as used herein means all the actions aimed at inhibiting the symptoms of angiogenesis-related diseases or obesity or delaying the progression by administering a composition of the present invention.

The term "treatment" as used herein means all the actions aimed at alleviating or improving the symptoms of angiogenesis-related diseases or obesity by administering a composition of the present invention.

The term "administration" as used herein means the introduction of a desired composition of the present invention into an individual in any appropriate way.

The term "individual" as used herein means all the animals which have an angiogenesis-related disease or a disease in which the symptoms of obesity may be alleviated, such as human, monkey, dog, goat, swine or mouse by administering a composition of the present invention to the animals.

The term "pharmaceutically effective amount" as used herein means an amount sufficient to treat a disease at a reasonable benefit/danger ratio applied for a medical treatment, and this may be determined depending on various factors known in the medical field, including the kind and severity of disease, drug activity, sensitivity, administration time, administration route and discharge ratio, administration time period, co-administered drugs, and others.

Hereinafter, the present invention will be described in detail.

The present invention provides an angiogenesis inhibitor containing one selected from the group consisting of Psoraleae Semen extract, Siegesbeckiae Herba extract, and Corni Fructus extract as an active ingredient.

The present invention also provides a method for inhibiting angiogenesis, including administering to an individual at least one selected from the group consisting of Psoraleae Semen extract, Siegesbeckiae Herba extract, and Corni Fructus extract.

A Psoraleae Semen extract, Siegesbeckiae Herba extract, and Corni Fructus extract of the present invention may be preferably prepared by a preparation method, including:

1) pulverizing each of dried Psoraleae Semen, Siegesbeckiae Herba, and Corni Fructus, followed by addition of an extraction solvent into each for extraction;

2) cooling down each of the extracts in Step 1, followed by filtration; and 3) evapoconcentrating each of the extracts in Step 2, followed by freeze-drying, but is not limited thereto.

Whether cultivated or commercially available, the Psoraleae Semen, Siegesbeckiae Herba, and Corni Fructus may be used without any limitation. The extracts of *Psoraleae* Semen, *Siegesbeckiae* Herba, and Corni Fructus according to the present invention may be prepared in the following manner. *Psoraleae* Semen, *Siegesbeckiae* Herba, and Corni Fructus are clearly washed with water, dried in the shade at room temperature and ground, placed into an extraction container, and extracted with an extraction solvent at an appropriate temperature for a predetermined time. A filter paper, etc. may be used to remove solid matters from the obtained extracts, the suspension may be centrifuged, and then a supernatant may be filtered under vacuum. The extraction solvent may be water, alcohol, or any mixture thereof, preferably one selected from $C_{1-4}$ lower alcohol or any mixture thereof, and more preferably ethanol, but is not limited thereto. The extraction solvent is added in an amount of 2 to 10 times by dried weight of the *Psoraleae* Semen, *Siegesbeckiae* Herba, and Corni Fructus. An extraction method including hot water extraction, immersion extraction, reflux cold extraction, and ultrasonic extraction may be used, and preferably a reflux cold extraction may be used 1 to 5 times. The extraction may be performed preferably at 50° C. to 100° C., more preferably at 50° C. to 60° C. The extraction may be performed for 1 to 7 hours, preferably for 5 hours.

In the preparation method, the evapoconcentrating in Step 3) may be performed preferably by an evaporator, and more preferably by rotary vacuum evaporator, but is not limited thereto. The concentrating under vacuum may be performed preferably at 20° C. to 60° C., and more preferably at 20° C. to 40° C., but is not limited thereto. The freeze-drying may be performed preferably by a freeze-dryer, more preferably by a vibration freeze-dryer, but is not limited thereto. The freeze-drying may be performed preferably at −50° C. to −100° C., and more preferably at −70° C., but is not limited thereto.

In a specific example of the present invention, the expression of cell adhesion promoting factors is concentration-dependently inhibited in the order of *Psoraleae* Semen>*Siegesbeckiae* Herba>Corni Fructus (See Tables 1 to 3 and FIGS. 2 to 4) within the range (See FIG. 1) that each extract of *Psoraleae* Semen, *Siegesbeckiae* Herba, and Corni Fructus does not exhibit the cytotoxicity. Each extract of the present invention concentration-dependently inhibited the expressions of signal transduction molecules β-catenin and vascular epithelium-cadherin (VE-cadherin); and a subgroup Akt (Protein kinase B), and inhibited a signal transduction therefrom and blocked the signal transduction until the NF-kB (See FIG. 9), and exhibited inhibitory effects of angiogenesis formation, which were much better than those of ECC as a positive control (See FIG. 5). The inhibition of angiogenesis formation from the inactivation of NF-kB by inhibiting a signal transduction was suggested.

Thus, the *Psoraleae* Semen extract, *Siegesbeckiae* Herba extract, and Corni Fructus extract of the present invention may be usefully used in angiogenesis inhibition and the prevention and treatment of angiogenesis-related diseases.

The present invention also provides a composition for prevention and treatment of angiogenesis-related diseases, containing one selected from the group consisting of *Psoraleae* Semen extract, *Siegesbeckiae* Herba extract, and Corni Fructus extract as an active ingredient.

The present invention also provides a method for preventing or treating angiogenesis-related diseases, including administering to an individual at least one selected from the group consisting of *Psoraleae* Semen extract, *Siegesbeckiae* Herba extract, and Corni Fructus extract.

The angiogenesis-related diseases include, but are not limited to, cerebrovascular disease, cardiovascular disease, ocular disease or cancerous disease.

Folkman (*PNAS* 99:10730-10735, 2002) reported that a mouse lost weight when an angiogenesis inhibitor was administered to the mouse, and Nishimura et al. (DIABETS, 56:1517-1526, 2007) revealed through laser confocal microscopy technology that angiogenesis was directly associated with preadipocyte differentiation in obesity tissues by a 3D-image analysis technique. It was previously asserted that preadipocytes played a leading role in angiogenesis by secreting various adipokines (VEGF, Leptin, TNF-a, and IL-6). However, Nishimura et al. disclosed that VEGF played a leading role in angiogenesis in adipose tissues. Therefore, a theory that obesity cell differentiation and proliferation may be prevented by inhibiting angiogenesis has been verified. Thus, an extract having angiogenesis inhibitory effects may be usefully used in treatment of obesity.

Vascular maturation means that blood vessels which have been formed become functionally mature while another angiogenesis is inhibited, and cerebrovascular maturation is summarized as a process in which a blood brain barrier is developed and a selective permeability is induced. While the blood brain barrier is developed, the angiogenesis in the brain is stopped and a capillary vessel is progressively differentiated into a blood brain barrier (Plate, K. H., *J. Neuropathol. Exp. Neurol.*, 58, 313-320, 1999). Because extracts of the present invention allow for a functional maturation through the generation of a blood brain barrier by inhibiting angiogenesis, the extracts may be usefully used as agents for treatment and prevention of blood brain barrier dysfunction-related diseases. The angiogenesis-related cerebrovascular diseases include, but are not limited to, multiple sclerosis (Rosenberg G A, Neuroscientist, 8(6):586-595, 2002), experimental allergic encephalomyelitis; Proescholdt M A et al., *J Neuropathol Exp Neurol.*, 61(10):914-925, 2002), bacterial meningitis, ischemia (Gashe Y et al., *J Cere Blood Flow Metab.*, 21(12):1393-1400, 2001), brain edema (Dempsey R J et al., *Neurosurgery.* 47(2):399-404; discussion 404-406, 2000), Alzheimer's disease (Banks W A et al., *Peptides,* 23(12):2223-2226, 2002), Acquired Immune Deficiency Syndrome dementia complex, brain tumor, traumatic brain injury; Esen F et al., *J Neurosurg Anesthesiol.*, 15(2):119-125, 2003), or hypertension (Kucuk M et al., *Life Sci.* 71(8): 937-946 2002).

The cardiovascular diseases may be selected from the group consisting of arteriosclerosis, vascular synechia, and scleredema (O'Brien K D et al., Circulation 93(4):672-682, 1996), and the ocular diseases may be selected from the group consisting of keratoplastic angiogenesis, angiogenic glaucoma, macular degeneration, diabetic retinopathy, premature infant retinopathy, angiogenic glaucoma, angiogenesis mediated cornea disease, macular degeneration, pterygium, retinal degeneration, retrolental fibroplasia, and granular conjunctivitis (Adamis A P et al., Angiogenesis, 3:9-14, 1999).

The cancerous diseases may be selected from the group consisting of astrocytoma, glioma, lung cancer, non-small cell lung carcinomas, hepatoma, colon carcinoma, bone cancer, pancreatic cancer, skin cancer, head or neck cancer, skin or intraocular melanoma, uterine cancer, ovarian cancer, rectal cancer, stomach cancer, cancer near the anus, colon carcinoma, breast cancer, fallopian tube carcinoma, endometrial carcinoma, cervical carcinoma, vaginal carcinoma, vulvar carcinoma, Hodgkin's disease, esophageal cancer, small intestine cancer, endocrine gland cancer, thyroid cancer, parathyroid cancer, adrenal cancer, soft tissue sarcoma, urethral cancer, penial cancer, prostatic cancer, bladder cancer, kidney or ureter cancer, renal cell carcinoma, pelvic carcinoma, central nervous system (CNS) tumor, primary CNS lymphoma, spinal cord tumor, and pituitary adenoma (Hanahan D et al., Cell, 86:353-364, 1996), and the composition of the present invention may be applied for the treatment of angiogenesis-related cancerous diseases and metastasis.

The composition of the present invention may further include one or more active ingredients having the same or similar functions. The composition of the present invention may also include one or more pharmaceutically acceptable carriers for administration. The composition of the present invention include about 0.0001% to about 10% by weight of the extract based on the total weight, and preferably 0.001% to about 1% by weight. The pharmaceutically acceptable carrier may be prepared by mixing more than one ingredient selected from the group consisting of saline, sterilized water, Ringer's solution, buffered saline, dextrose solution, malto-dextrose solution, glycerol and ethanol. If necessary, anti-oxidative agent, buffer solution, bacteriostatic agent, and other conventional additive may be added. Diluents, dispersing agents, surfactants, binders and lubricants may be additionally added to prepare injectable solutions, pills, capsules, granules or tablets. The composition of the present invention may further be preferably prepared for each disease or according to ingredients by following suitable methods in the art.

The composition of the present invention may be administered orally or parenterally (for example, intravenous, hypodermic, peritoneal or local application). The effective dosage of the composition may be determined according to weight, age, gender, health condition, diet, administration time, administration method, excretion ratio and severity of a disease. The dosage of the present invention is about 0.01 to about 5,000 mg/kg per day, and preferably about 0.01 to about 10 mg/kg per day. The composition is administered once a day or preferably a few times a day.

The present invention also provides a composition for inhibition of obesity, containing *Psoraleae* Semen extract or *Siegesbeckiae* Herba extract as an active ingredient.

The present invention also provides a method for inhibiting obesity, including administering to an individual an effective amount of *Psoraleae* Semen extract or *Siegesbeckiae* Herba extract.

Figure 11:
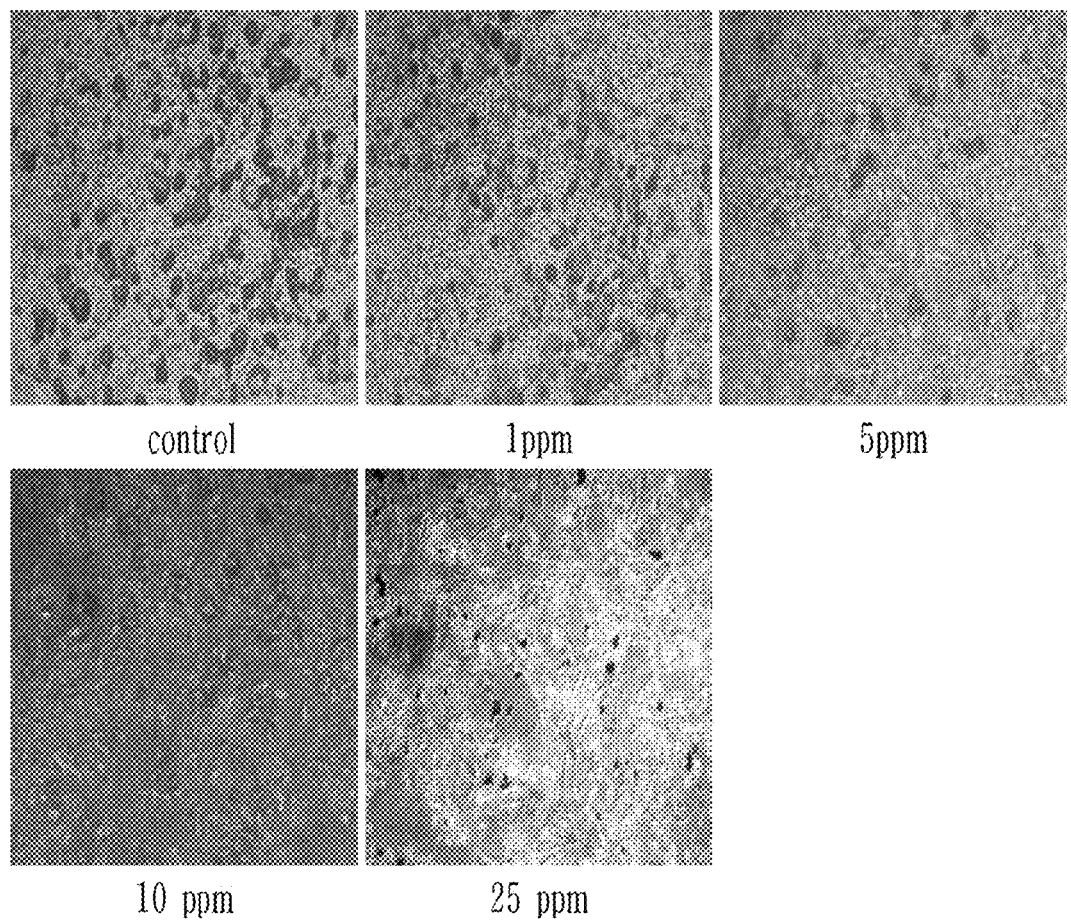
FIGS. 11 through 13 are groups of photos illustrating inhibitory effects of each extract of Psoraleae Semen, Siegesbeckiae Herba, and Corni Fructus of the present invention on adipocytes.
Figure 12:
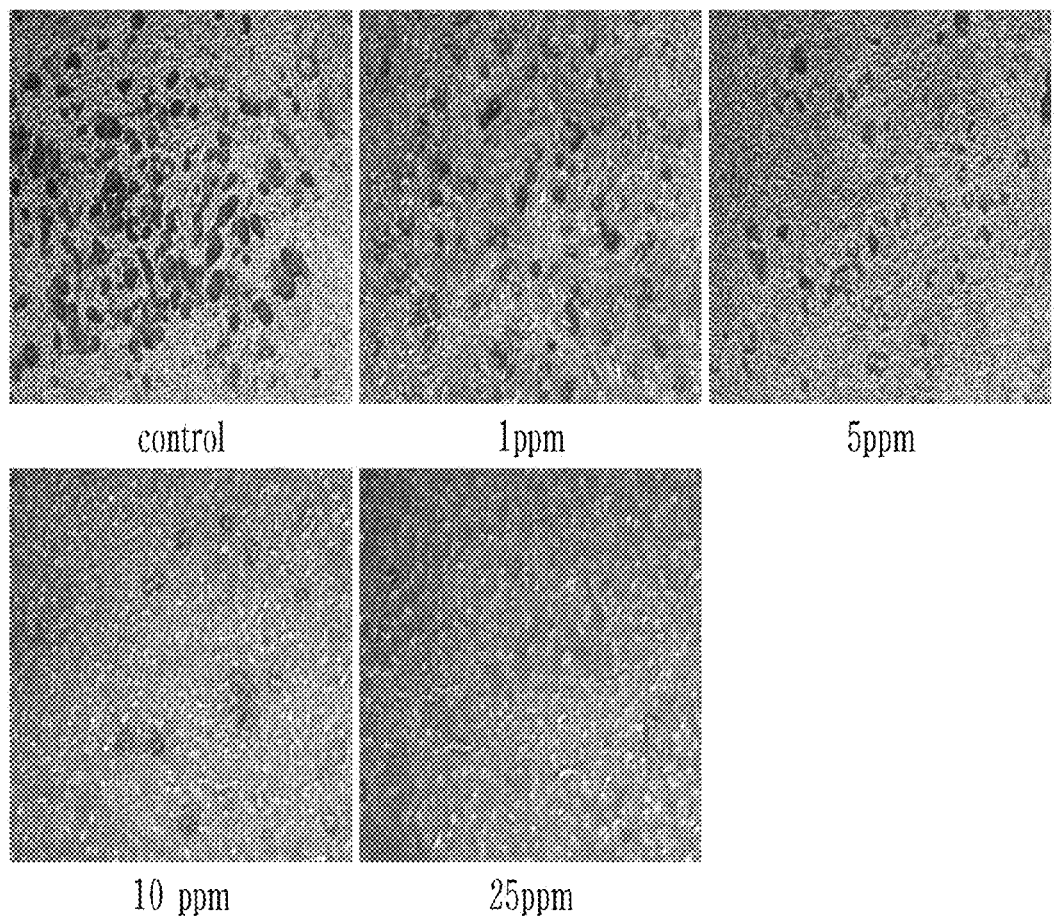

In a specific example of the present invention, the *Psoraleae* Semen extract or *Siegesbeckiae* Herba extract of the present invention concentration-dependently decreased adipose cells (See FIGS. 11 and 12). In addition, the *Psoraleae* Semen extract or *Siegesbeckiae* Herba extract of the present invention concentration-dependently decreased the expression of PPARγ, a signal molecule which mediates the expression of lipogenesis, during an adipocyte differentiation process, and decreased the expressions of SREBP-1 and PPARγ, signal molecules which mediate lipogenesis even after a complete differentiation of adipocytes (See FIGS. 15 and 16). The *Psoraleae* Semen extract or *Siegesbeckiae* Herba extract of the present invention decreased the weight in an animal experiment when ingested with a high fat diet (See FIG. 17), and significantly decreased the levels of total serum cholesterol and neutral fat (See FIG. 4). Because *Psoraleae* Semen, *Siegesbeckiae* Herba, and Corni Fructus extracts of the present invention have effects of lipogenesis inhibition and adipogenesis inhibition, decrease weight, and decrease the levels of total serum cholesterol and neutral fat, the extracts may be usefully used for inhibition of obesity.

The present invention also provides a health supplement food for preventing or improving antiogenesis-related diseases, containing one selected from the group consisting of *Psoraleae* Semen extract, *Siegesbeckiae* Herba extract, and Corni Fructus extract as an active ingredient.

Furthermore, the present invention provides a health supplement food for preventing or improving obesity, containing *Psoraleae* Semen extract or *Siegesbeckiae* Herba extract as an active ingredient.

The *Psoraleae* Semen extract or *Siegesbeckiae* Herba extract of the present invention may be directly added, used with other foods or food ingredients, and suitably used according to conventional methods. The mixed amount of the active ingredients may be suitably determined according to the purpose of use (prevention, health, or sanitation). In general, the *Psoraleae* Semen extract or *Siegesbeckiae* Herba extract of the present invention may be added in an amount of about 15 parts by weight or less with respect to raw material, and preferably about 10 parts by weight or less. However, the amount may be below the above range in the case of a long-term administration for health or sanitation, or health management. Because there is no safety issues regarding the extracts, the active ingredient may be used more than the above ranges.

There are no specific limitations regarding the form and kind of the health supplement food. The health supplement food into which the *Psoraleae* Semen extract or *Siegesbeckiae* Herba extract may be added may be in a form of tablet, capsule, powder, granule, liquid, and pill. The health supplement food includes milk products including butter, yogurt, and cheese, dairy products including ice cream, bread, chocolate, candies, snacks, confections, ramyon (instant noodles), other noodles, gums, various soups, beverage, tea, drinks, alcoholic beverage, and vitamin complex, and all the health supplement foods in a conventional sense.

The health supplement food of the present invention may contain various flavors or natural carbohydrate as additional ingredients just like conventional health supplement foods. The above natural carbohydrate includes monosaccharide such as glucose and fructose, disaccharide such as maltose and sucrose, polysaccharide such as dextrin and cyclodextrin, and sugar alcohol such as xylitol, sorbitol, and erythritol. Sweeteners may include natural sweeteners such as thaumatin and stevia extract, and synthetic sweeteners such as saccharin and aspartame. The content of the natural carbohydrate may be generally about 0.01 g to about 0.04 g per 100 Ml of the *Psoraleae* Semen extract or *Siegesbeckiae* Herba extract of the present invention, and preferably about 0.02 g to about 0.03 g.

In addition to the above, the health supplement food may contain various kinds of nutrient, vitamin, electrolyte, flavoring agent, coloring agent, pectic acid and salt thereof, organic acid, preventive colloidal thickener, pH modifier, stabilizer, antiseptic, glycerin, alcohol, carbonation reagent used in the preparation of carbonated beverage, etc. In addition, the *Psoraleae* Semen extract or *Siegesbeckiae* Herba extract of the present invention may contain flesh of fruits to prepare natural fruit juice, fruit juice beverage, and vegetable beverage. These components may be used alone or in combination with other components. Although the content of these additives does not matter, the additives may be used in the range of about 0.01 to about 0.1 parts by weight per 100 parts of the composition of the present invention.

Hereinafter, the present invention will be described in more detail with reference to the following examples and experimental examples.

However, the following examples and experimental examples are provided for illustrative purposes only, and the scope of the present invention should not be limited thereto in any manner.

Example 1

Preparation of Extracts of *Psoraleae* Semen, *Siegesbeckiae* Herba, and Corni Fructus

*Psoraleae* Semen, *Siegesbeckiae* Herba, and Corni Fructus obtained from an herbal medicine shop (Daejeon, Korea) were confirmed through a comparative test of their external features by the Herbal Quality Control Team in Korea Institute of Oriental Medicine (KIOM) and then used in an experiment. The *Psoraleae* Semen, *Siegesbeckiae* Herba, and Corni Fructus were washed, completely dried by a dryer, and cut into small pieces for use.

<1-1> Preparation of Water Extract 600 g of each chopped natural product was immersed in 5 times volume of water and hot water extracted for 5 hours. The extract was cooled down, subjected to a filtration process to obtain a supernatant, which was concentrated by an evaporator, and subjected to a freeze-drying to concentrate the extract. 120 g (20%) of the extract was obtained.

<1-2> Preparation of Ethanol Extract 600 g of each chopped natural product was immersed in 5 times volume (3,000 Ml) of 70% ethanol, the mixture was refluxed for 5 hours while heating, and an extract was obtained. The extraction process was 2 times repeated, and the extract was cooled down and subjected to a filtration process to obtain a supernatant, which was later concentrated by an evaporator and subjected to a freeze-drying to concentrate the extract. 90 g of the extract was obtained.

<1-3> Preparation of Methanol Extract

100% methanol was used in the same way as in Example 1-2 to obtain 100 g of an extract.

Experimental Example 1

Confirmation of Cell Adhesion Inhibitory Effects

<1-1> Confirmation of Cytotoxicity

HUVEC (Young Science, Korea) was seeded at $1 \times 10^4$ cells/well in a 96-well plate, incubated in EBM-2 medium (Cambrex, USA) supplemented with 2% FBS at 37° C. in a 5% $CO_2$-incubator, and further incubated until the maximum is reached. Subsequently, the extract in Example 1 was added at each concentration into the medium and incubated for 48 hours. Next, the medium in the culture solution was decanted, 1 Ml of 0.1 mM MTT was added, the mixture was incubated for another 4 hours, and the medium was removed. 200 µl of DMSO was aliquoted into each well and the absorbance was measured at 570 nm.

As a result, as illustrated in FIG. 1, *Psoraleae* Semen, *Siegesbeckiae* Herba, and Corni Fructus did not exhibit the cytotoxicity until 10 ppm, 25 ppm, 25 ppm, respectively (FIG. 1).

<1-2> Confirmation of Cell Adhesion Factors

HUVEC (Young Science, Korea) was seeded at $5 \times 10^3$ cells/well in a 96-well plate, incubated in EBM-2 medium supplemented with 2% FBS at 37° C. in a 5% $CO_2$-incubator, and further incubated until the maximum is reached. Subsequently, the extract in Example 1 was added at each concentration into the medium within the range of the cytotoxicity not observed and incubated for 20 hours. Next, the culture solution was washed with PBS, IL-1β (Endogen, USA) was added at 5 ng/Ml in order to induce cell adhesion factors, and then the mixture was incubated for 6 hours. The medium was removed, 1% paraformaldehyde was added, and a reaction was performed for 30 min to fix cells. After 30 min, the mixture was twice washed with PBS+0.5% Tween 20 and blocked with 10% FBS for 1 hour. Monoclonal antibodies (VCAM-1, ICAM-1, and E-selectin: BD Bioscience, USA) were dissolved in PBS supplemented with 10% FBS at 2, 5, and 5 µg/Ml respectively at 37° C. for 2 hours, and were washed with PBS+0.5% Tween 20. A secondary antibody (Donkey anti-mouse IgG-HRP: Bio-Rad, USA) was 1000-fold diluted in PBS supplemented with 10% FBS at room temperature for 1 hour, a coloring agent (Western Blotting Luminol Reagent: Bio-Rad, USA) was added into the dilution, reaction was performed for 1 hour, and then the absorbance was measured at 405 nm on a plate reader (UVM 340, ASYS, Australia).

As a result, as illustrated in Tables 1 to 3, it was observed that the ethanol extract among the water, ethanol, and methanol extracts sufficiently inhibited the cell adhesion promoting factors VCAM-1, ICAM-1, and E-selectin. Thus, a subsequent experiment was performed with an ethanol extract (See Tables 1 to 3).

TABLE 1

Inhibition rates of VCAM-1 by *Psoraleae* Semen, *Siegesbeckiae* Herba, and *Corni Fructus*

| Sample | Concentration (ppm) | Water Extract | Ethanol Extract | Methanol Extract |
|---|---|---|---|---|
| Negative control (physiological saline solution) | — | — | — | — |
| *Psoraleae Semen* | 1 | 98.2% | 100.0% | 95.0% |
| *Siegesbeckiae Herba* | 5 | 110.0% | 114% | 102.0% |
| *Corni Fructus* | 5 | 100.0% | 111.8% | 98.7% |

TABLE 2

Inhibition rates of ICAM-1 by *Psoraleae* Semen, *Siegesbeckiae* Herba, and *Corni Fructus*

| Sample | Concentration (ppm) | Water Extract | Ethanol Extract | Methanol Extract |
|---|---|---|---|---|
| Negative control (physiological saline solution) | — | — | — | — |
| *Psoraleae Semen* | 1 | 98.0% | 100.0% | 95% |
| *Siegesbeckiae Herba* | 5 | 128% | 136% | 110% |
| *Corni Fructus* | 5 | 65.0% | 66.7% | 63.2% |

TABLE 3

Inhibition rates of E-selectin by *Psoraleae* Semen, *Siegesbeckiae* Herba, and *Corni Fructus*

| Sample | Concentration (ppm) | Water Extract | Ethanol Extract | Methanol Extract |
|---|---|---|---|---|
| Negative control (physiological saline solution) | — | — | — | — |
| *Psoraleae Semen* | 1 | 120% | 128.0% | 105% |
| *Siegesbeckiae Herba* | 5 | 115% | 120.0% | 100% |
| *Corni Fructus* | 5 | 97.5% | 100.7% | 96.0% |

Figure 2:
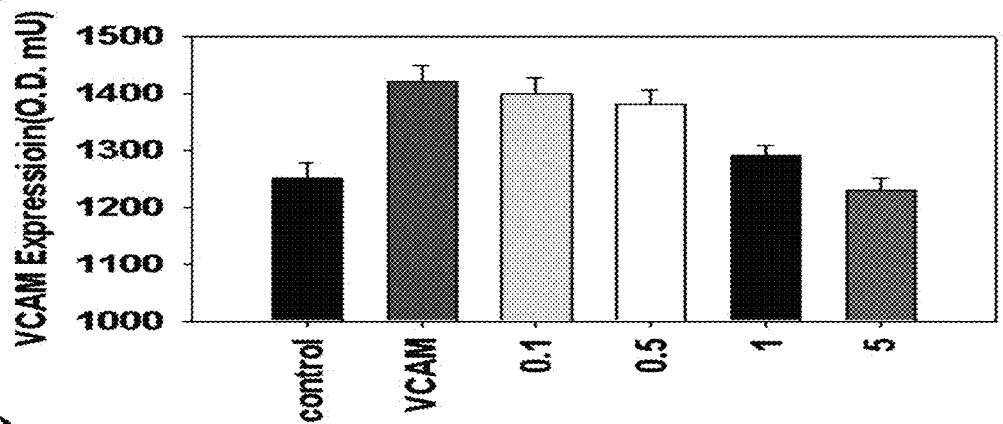
FIG. 2 is a group of graphs illustrating inhibitory effects of each extract of Psoraleae Semen, Siegesbeckiae Herba, and Corni Fructus on a cell adhesion promoting factor VACM-1.
Figure 2:
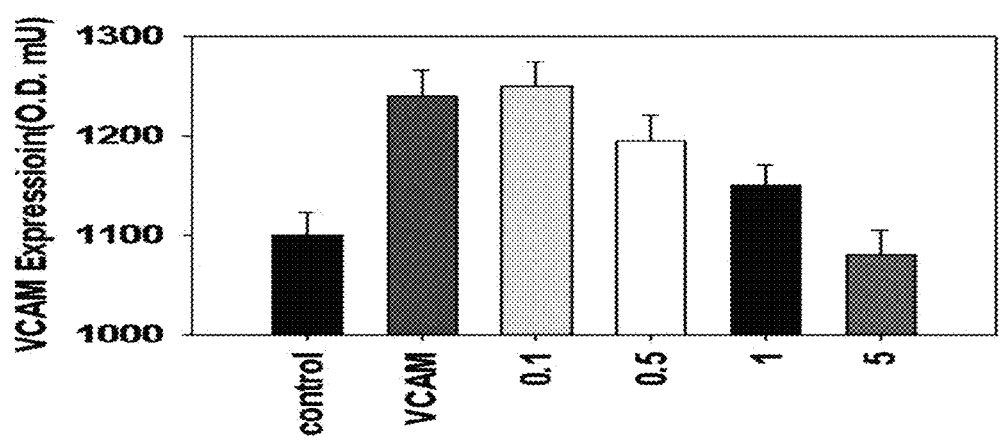
Figure 2:
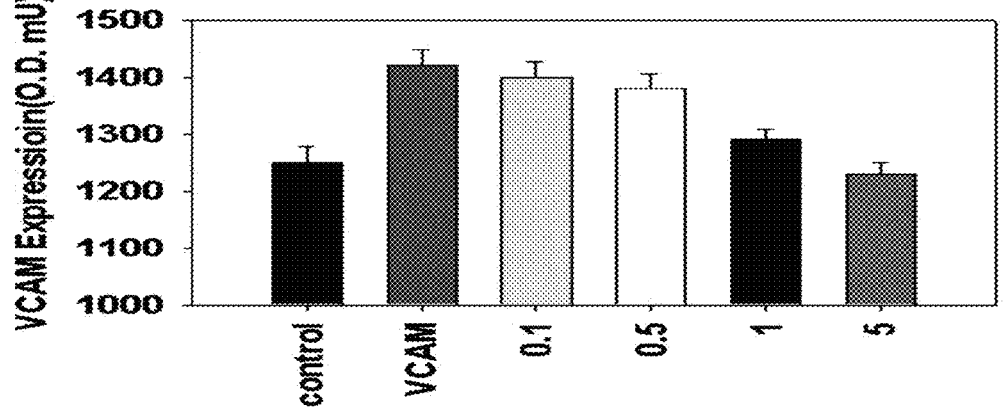
Figure 3:
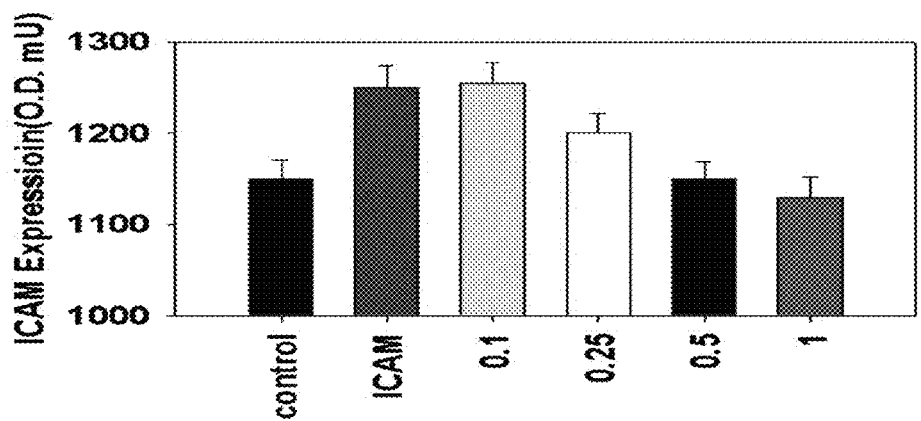
FIG. 3 is a group of graphs illustrating inhibitory effects of each extract of Psoraleae Semen, Siegesbeckiae Herba, and Corni Fructus on a cell adhesion promoting factor IACM-1.
Figure 3:
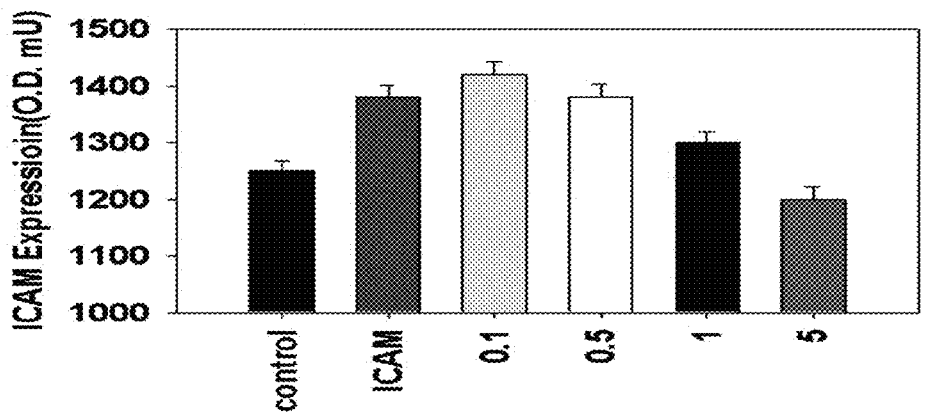
Figure 3:
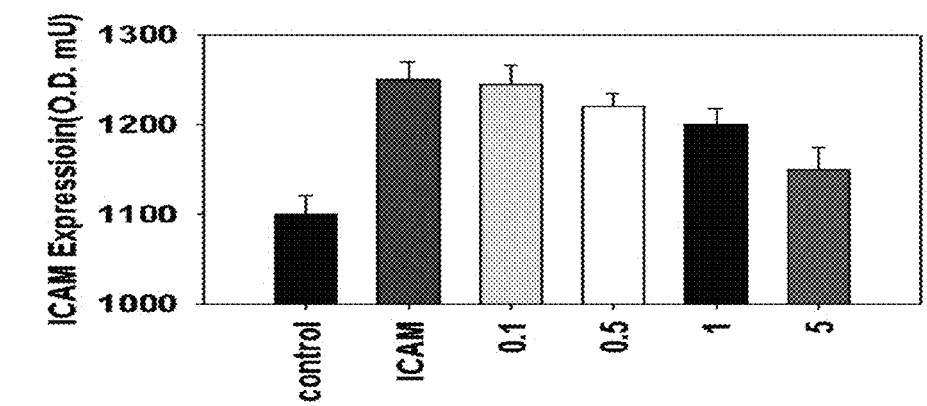
Figure 4:
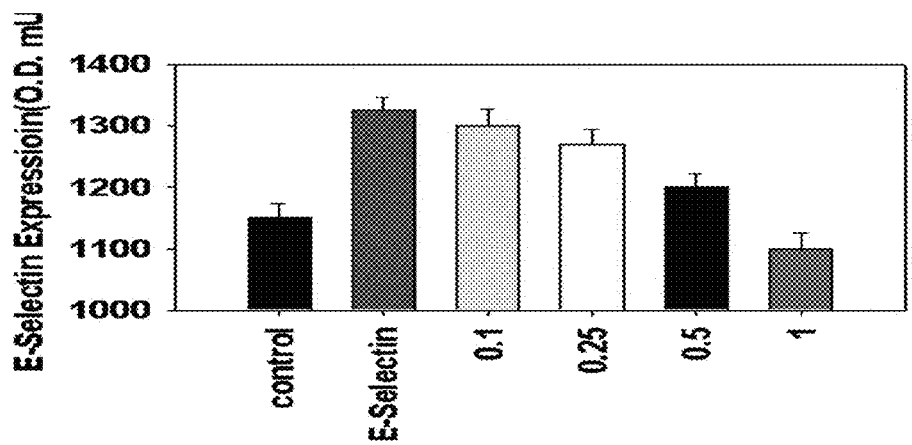
FIG. 4 is a group of graphs illustrating inhibitory effects of each extract of Psoraleae Semen, Siegesbeckiae Herba, and Corni Fructus on a cell adhesion promoting factor E-selectin.
Figure 4:
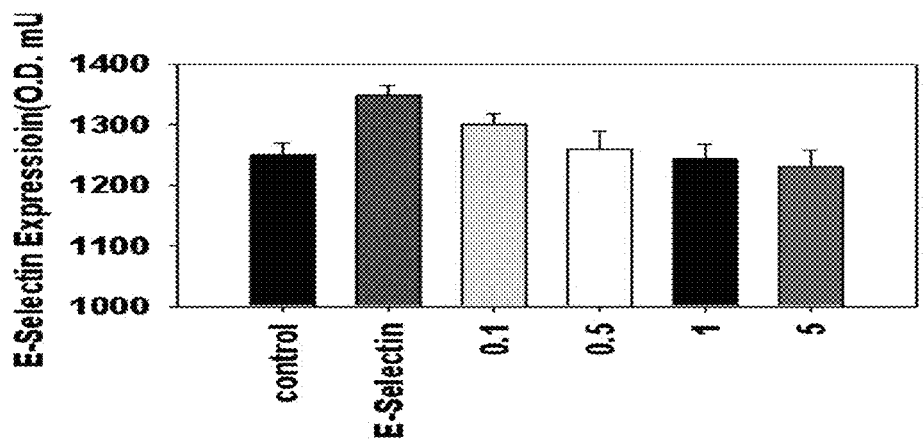
Figure 4:
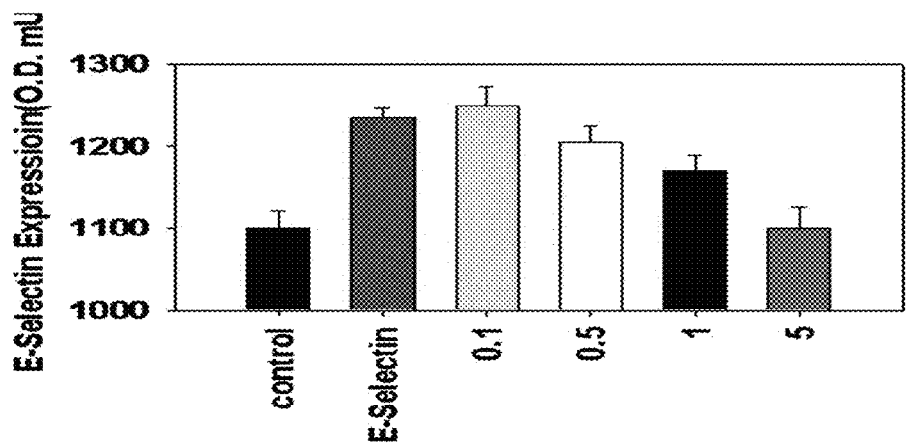

As a result, aS illustrated in FIGS. 2 to 4, each extract of *Psoraleae* Semen, *Siegesbeckiae* Herba, and Corni Fructus concentration-dependently inhibited the expressions of cell adhesion promoting factors VCAM-1, ICAM-1, and E-selectin. Specifically, *Psoraleae* Semen, *Siegesbeckiae* Herba, and Corni Fructus exhibited significantly lower inhibitory effects in the case of VCAM-1 at 1.0 ppm, 5.0 ppm, and 5.0 ppm, respectively compared to a control group, and it was confirmed that the inhibitory strengths were in the order of *Psoraleae* Semen (0.5 ppm, 100%)>*Siegesbeckiae* Herba (5.0 ppm, 114%)>Corni Fructus (5.0 ppm, 111.8%). It was observed in the case of ICAM-1 that the inhibitory strengths were in the order of *Psoraleae* Semen (0.5 ppm, 100%) >*Siegesbeckiae* Herba (5.0 ppm, 138%)>Corni Fructus (5.0 ppm, 66.7%), while it was observed in the case of E-selectin that the inhibitory strengths were in the order of *Psoraleae* Semen (1.0 ppm, 128%)>*Siegesbeckiae* Herba (5.0 ppm, 120%)>Corni Fructus (5.0 ppm, 100.7%). In conclusion, it was confirmed that the inhibitory strengths were in the order of *Psoraleae* Semen (5.0 ppm)>*Siegesbeckiae* Herba (0.5 ppm)>Corni Fructus (5.0 ppm) (FIGS. 2 to 4).

Experimental Example 2

Confirmation of Inhibitory Effects of Angiogenesis

150 µl of matrigel was added into a 24-well plate (Becton Dickinson Labware, USA) to coat the surface and allowed to stand at 37° C. for 1 hour for solidification. Cells ($2.5 \times 10^4$ cells/well) separated by adding trypsin-EDTA into the well plate were aliquoted, the extracts in Example 1 were administered at each concentration into the aliquots, and the mixtures were incubated under 37° C. and 5% $CO_2$ conditions for 4 hours. Subsequently, once tube networks were formed, five samples were randomly selected and photographed by a digital camera (Coolpix; Nikon, Japan) to obtain images, and tube lengths were measured by an NIH image program.

Figure 5:
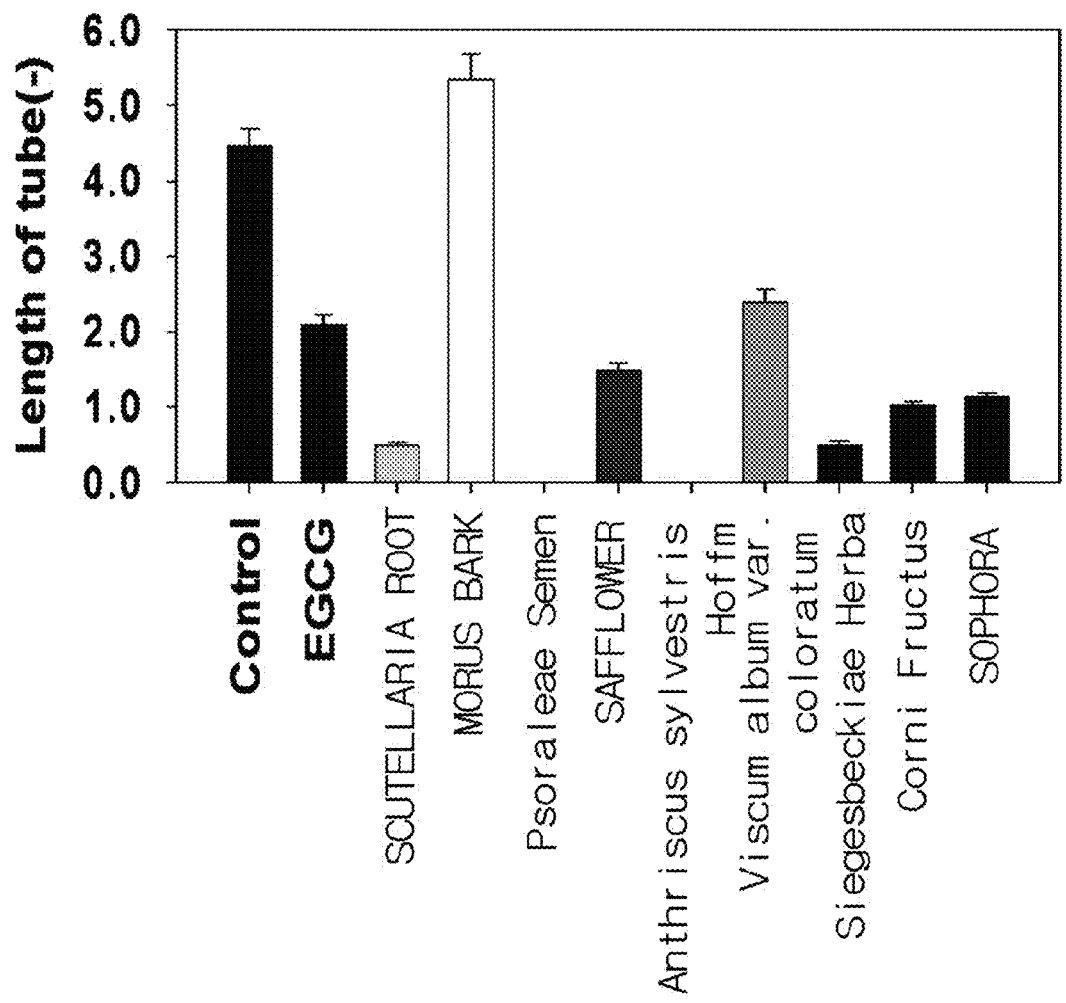
FIG. 5 is a graph illustrating angiogenesis inhibitory effects by each extract of Psoraleae Semen, Siegesbeckiae Herba, and Corni Fructus.

As a result, as illustrated in FIG. 5, it was confirmed that the angiogenesis inhibitory effects by *Psoraleae* Semen, *Siegesbeckiae* Herba, and Corni Fructus extracts were excellent compared to those by EGCG as a negative control (FIG. 5).

Experimental Example 3

Confirmation of Angiogenesis Inhibitory Mechanisms

In order to understand the angiogenesis inhibitory mechanisms by *Psoraleae* Semen, *Siegesbeckiae* Herba, and Corni Fructus extracts, the present inventors examined signal transduction molecules β-catenin and vascular epithelium-cadherin (VE-cadherin); and the subgroup Akt (Protein kinase B) to study the actions of the extracts.

<3-1> Extract Processing and VEGF Stimulation

Specifically, $1 \times 10^5$ cells of HUVEC were inoculated into a 100 mm petri-dish and incubated. When the maximum was reached, the extracts in Example 1 were processed at each concentration, incubated for 24 hours, and washed with serum-free EBM-2 medium. The processed group was incubated overnight without addition of serum, VEGF (BD Science, USA) was added at a final concentration of 50 ng/Ml and a reaction was performed at 37° C. for 30 min.

<3-2> Protein Isolation and Immunoprecipitation

In order to prevent phosphorylation, vanadate (100 µM) and hydrogen peroxide (200 µM) were added for 7 min prior to the lysis of cells. Subsequently, cells were washed with PBS+0.1 mM $Na_3VO_4$, which was immediately cooled down, and a cooled lysis buffer [150 mM NaCl, 10 mM Tris-HCl (pH 7.4), 1% Triton X-100, 1 mM vanadate, 1 mM EDTA, 1 mM FGTA, 0.2 mM PMSF, 0.5% NP-40] was added to perform a reaction at 4° C. for 20 min. Next, cells were harvested with a stripper and introduced into a microependorf tube, followed by centrifugation at 4° C. and 14,000 rpm for 10 min. The concentrations of proteins in the supernatant were quantified by using a BCA protein test kit (Pierce, USA), and immunoprecipitations were performed by using an anti-VE-Cadherin antibody (BD Bioscience, USA). 50 µg of the proteins and 10 µl of the antibody were added into 500 µl of immunoprecipitation buffer (supplemented with 0.2 mM sodium vanadate), and then $H_2O$ was added to make 1 Ml as the total volume. After the working solution was vortexed, a reaction was performed at 4° C. for 12 hours and 20 µl of protein A/G-agarose (Amersham Science, Sweden) was added. After another reaction at 4° C. for 30 min, a centrifugation was performed at 4° C. and 14,000 rpm for 3 min to remove the supernatant. The solution was washed with 500 µl of a washing buffer and then subjected to a centrifugation to remove the supernatant.

<3-3> Western Blotting

50 µl of 4× Laemmli sample loading buffer was added into a purified protein and boiled at 95° C. for 5 min. The sample was subjected to electrophoresis with 7% SDS-PAGE gel and transferred to 0.2 µm nitrocellulose membrane (Bio-Rad Lab. USA). The protein transferred into the membrane was identified with a Ponceau-S (Markham, Canada) reagent, blocked with 5%-non-fat dry milk (NFDM), and each treated with primary antibodies anti-β-catenin, anti-Akt, anti-VE-cadherin, and anti-β-actin (BD Bioscience, USA), respectively. A secondary antibody donkey anti-goat IgG-HRP was diluted at a ratio of 1:7000 for reaction and was exposed to a film by using ECL (Santa Cruz Biotechnology, USA) as a fluorescent material.

Figure 6:
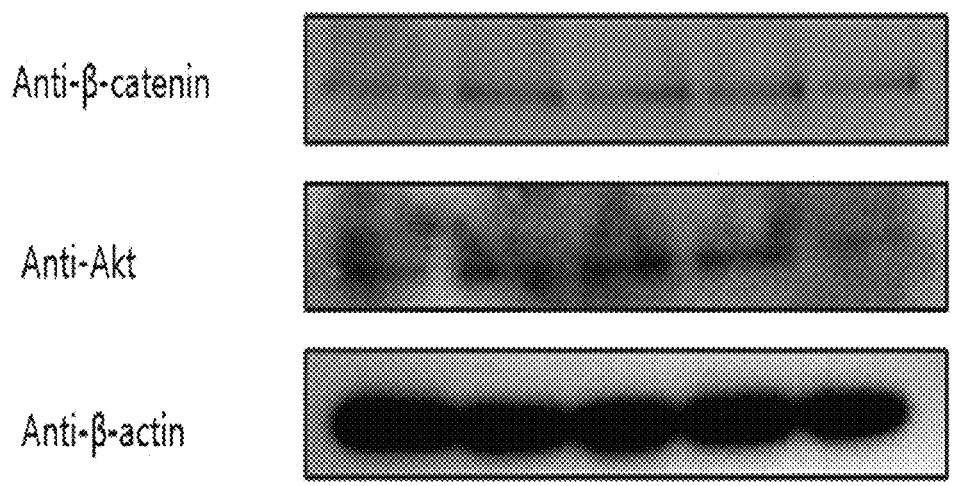
FIGS. 6 through 8 are a group of photos illustrating expression-inhibitory effects of each extract of Psoraleae Semen, Siegesbeckiae Herba, and Corni Fructus on signal transduction molecules.
Figure 7:
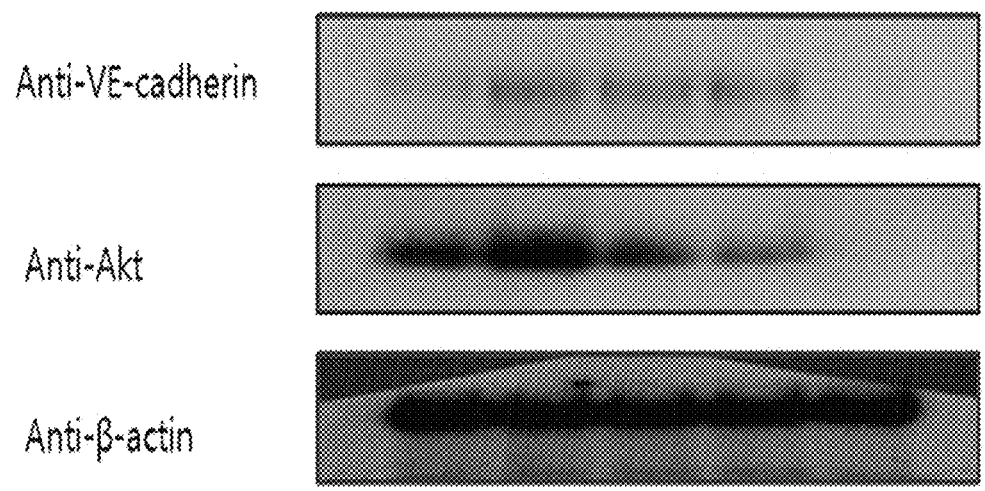
Figure 8:
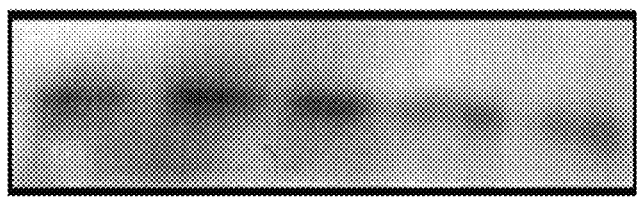
Figure 8:
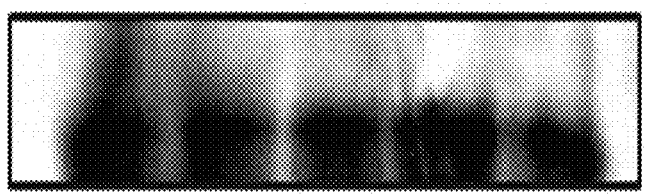
Figure 9:
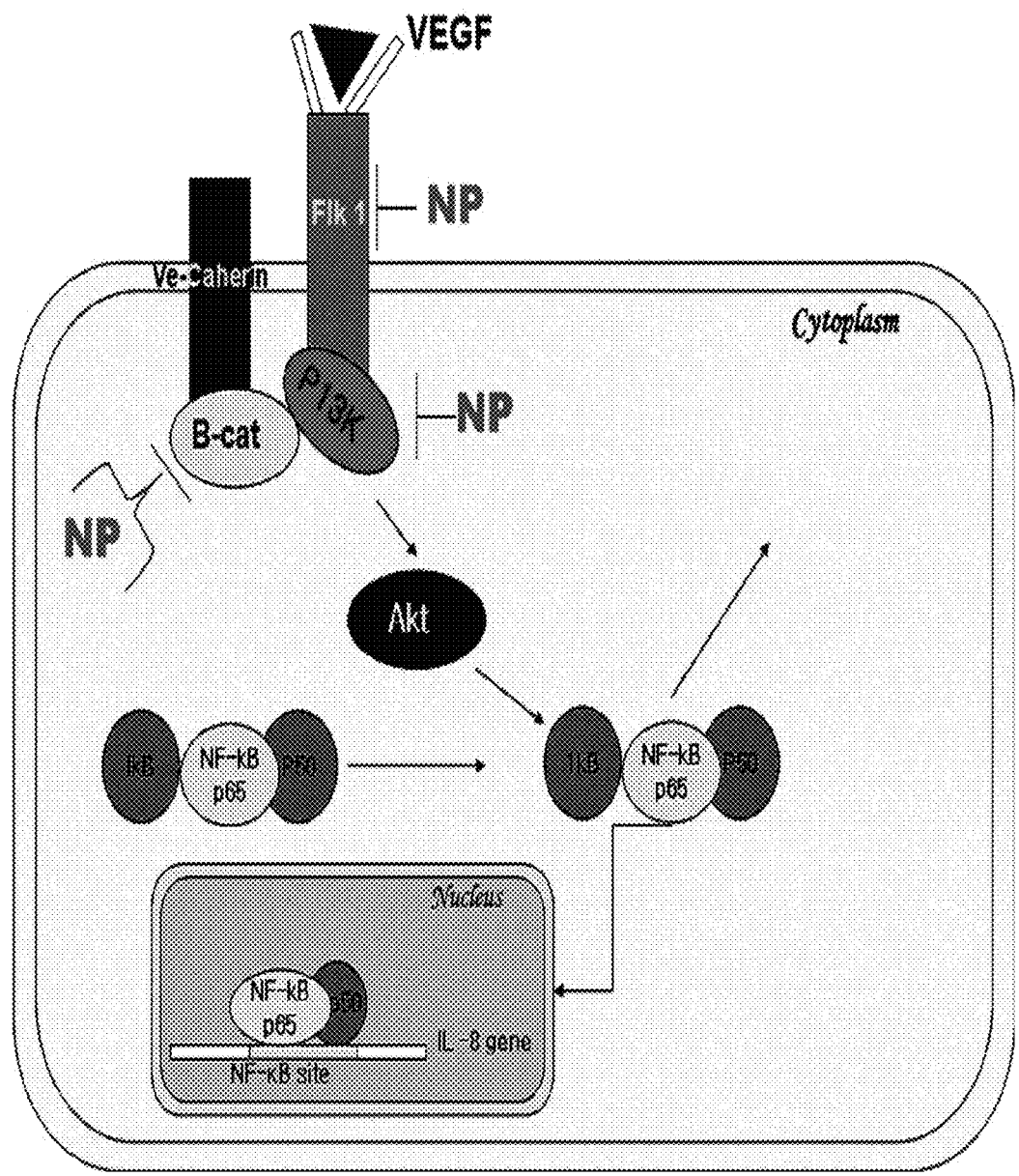
FIG. 9 is a view illustrating the signal transduction pathway of a signal transduction molecule into an NF-kB.

As a result, as illustrated in FIGS. 6 and 7, it was confirmed that the detection signals of the antibodies decreased as the concentrations of the extracts (FIGS. 6 and 7). From these, the extracts concentration-dependently inhibited the expression of a signal transduction molecule, and the inhibition of the signal transduction prevented the signal transduction molecule from being transferred to the NF-kB (FIG. 9). Thus, it was proposed that the inactivation of the NF-kB inhibit angiogenesis.

Experimental Example 4

Confirmation of In Vivo Angiogenesis Inhibitory Effects of Natural Products by a Chorioallantoic Membrane (CAM) Test After a fertilized egg was grown in a 37° C. incubator in which the humidity of 70% or more was maintained for 3 days and perforated, 4 Ml of albumin was withdrawn by a syringe. When the fertilized egg became an embryo at day 4, a round window was drilled on an upper part of the air sac in the fertilized egg and a transparent tape was put on the part. In order to observe the angiogenesis inhibitory effects, 200 µl of *Psoraleae* Semen, *Siegesbeckiae* Herba, and Corni Fructus extracts at 10, 25, and 25 ppm, respectively were applied to 13 mm-diameter thermatox coverslips and dried. When the embryo was grown for 4.5 days, the transparent tape was detached, these coverslips were placed on the surface of chorioallantoic membrane (CAM) of a developing embryo, and then the window was blocked with the transparent tape. A thermatox coverslip was only attached on the chorioallantoic membrane (CAM) of chick embryo as a control group. After this was incubated in an incubator for 2 days, 10% fat emulsion was injected with a syringe into the chorioallantoic membrane (CAM) and the angiogenesis process was observed. 60 or more chorioallantoic membranes of chick embryo were used for each experimental group and photographed by a digital camera to obtain their images.

Figure 10:
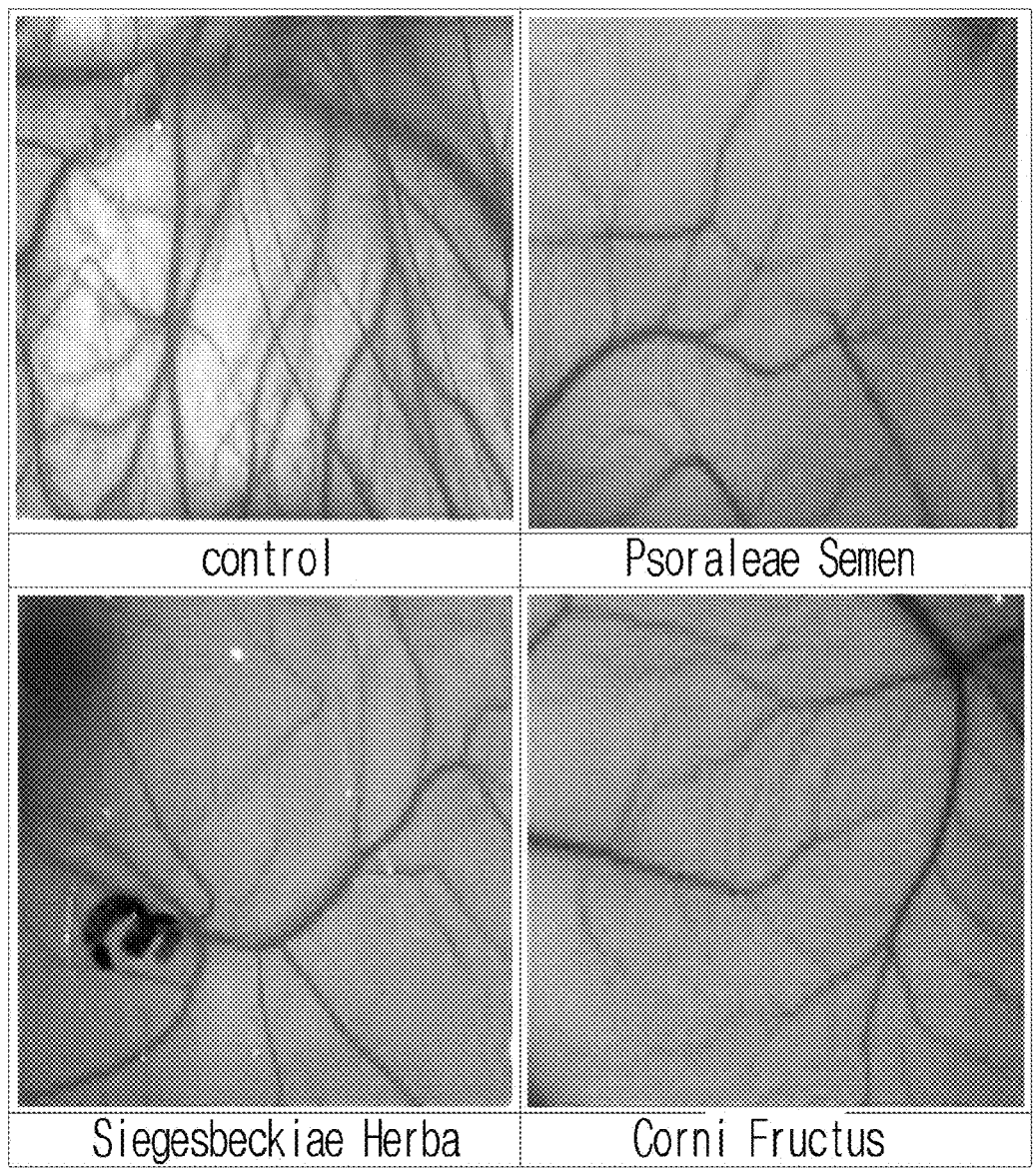
FIG. 10 is a group of photos illustrating in vivo inhibitory effects of each extract of Psoraleae Semen, Siegesbeckiae Herba, and Corni Fructus of the present invention on angiogenesis.

As a result, as illustrated in FIG. 10, it was confirmed that the extract of the present invention significantly inhibited in-vivo angiogenesis (FIG. 10).

Experimental Example 5

Confirmation of Adipocyte Inhibitory Effects

3T3-L1 preadipocytes were incubated in a DMEM/10% FBS medium until the bottom of the flask was covered with the cells, and further incubated for another 2 days. An induction medium (MDI, 0.5 mM 3-isobutyl-1-methylxanthine, 0.5 μM dexamethasone, 10 μg/Ml insulin) was placed into the culture for incubation to induce the differentiation of the preadipocytes into the adipocytes. The medium was exchanged with a normal DMEM/10% FBS medium on day 3, and *Psoraleae* Semen, *Siegesbeckiae* Herba, and Corni Fructus extracts were processed at each concentration for 7 to 10 days while the media were exchanged once in two days.

In order to analyze the differentiation into the adipocytes, the incubated cells were fixed with formalin. After the formalin was removed, the cells were washed with 60% isopropanol and dried until white kernels appeared. After the cells were stained with oil-red and a working solution, the staining solution was removed and washed four times with distilled water. After a staining solution on non-fat portions was washed with 100% isopropanol, a stained intracellular fat was observed under microscope.

Figure 13:
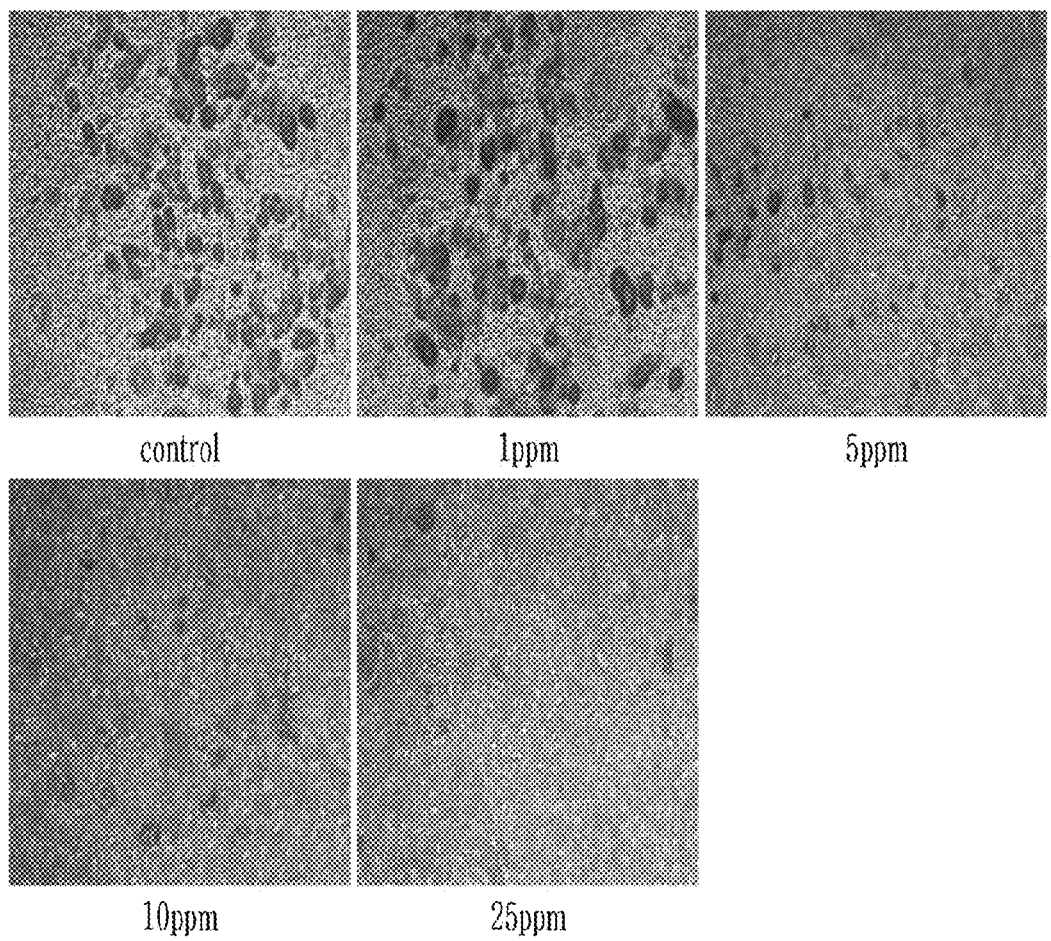

As a result, as illustrated in FIGS. 11 to 13, it was observed that *Psoraleae* Semen, *Siegesbeckiae* Herba, and Corni Fructus extracts significantly decreased adipocytes in a concentration-dependent manner (FIGS. 11 to 13).

Experimental Example 6

Lipogenesis and Adipogenesis Inhibitory Effects

Figure 14:
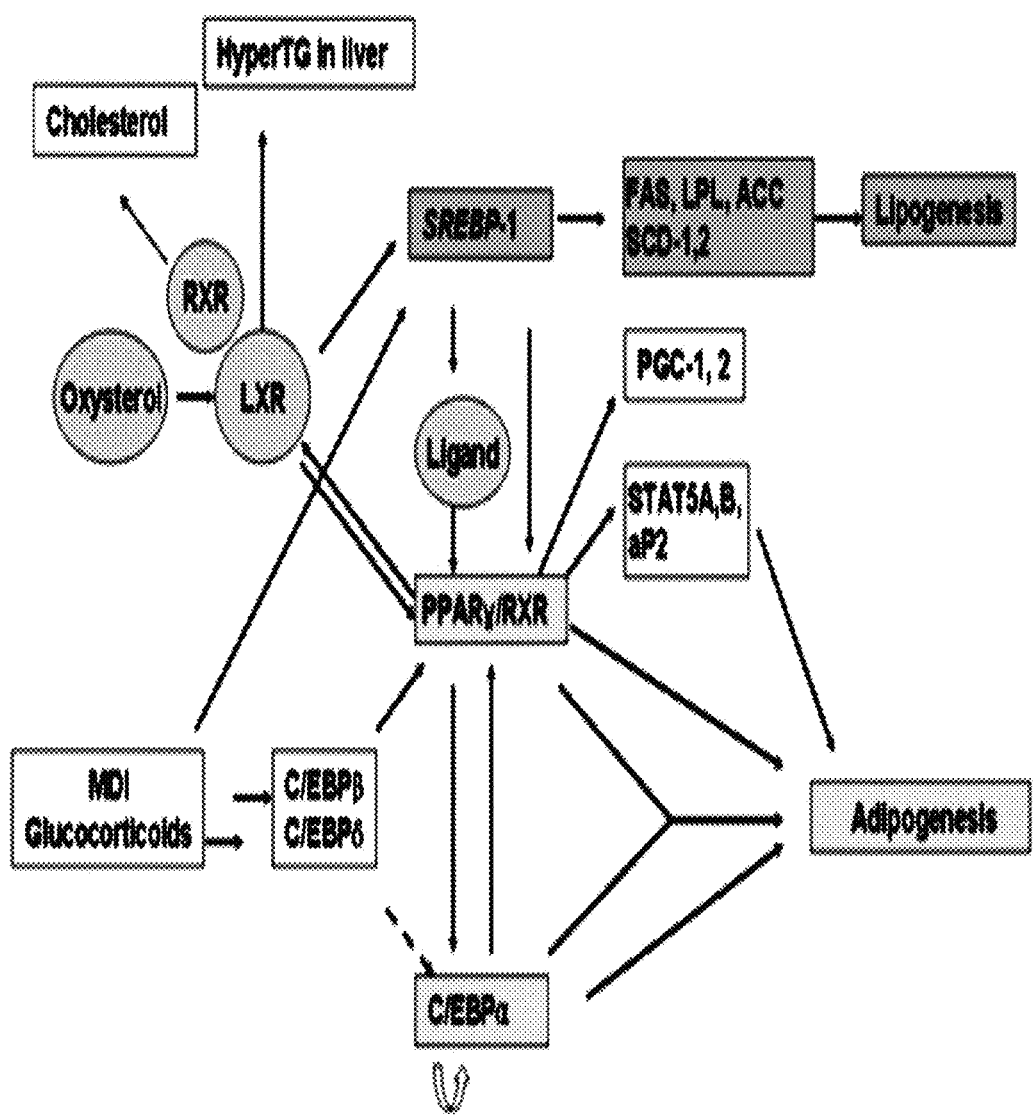
FIG. 14 is a view illustrating the control of lipogenesis and adipogenesis by signal transduction molecules SREBP-1 and PPARγ.

In order to confirm the degrees of adipogenesis and lipogenesis inhibition by *Psoraleae* Semen, *Siegesbeckiae* Herba, and Corni Fructus extracts at the protein level, the present inventors performed a Western blot. In order to confirm the inhibitions of lipogenesis and adipogenesis by two signal molecules associated with the lipogenesis signal pathway, the present inventors used SREBP-1 (SC-367) and PPARγ(SC-7273) antibodies to perform a Western blot on a group in which a differentiation material and a sample were simultaneously introduced and a group in which a sample was introduced after a differentiation was induced, respectively (FIG. 14).

<6-1> 3T3-L1 Cell Differentiation and Sample Treatment

After 3T3-L1 cells were pre-incubated to fill a T-75 flask, the cells were trypsinized to aliquot $1 \times 10^5$ cells on each p100 dish. DMEM containing 10% BS was added into the dishes to make 10 Ml as a total volume and the incubation was performed at 37° C. under 5% $CO_2$ conditions When cells were fully incubated, they were incubated for two more days. A first group was simultaneously treated with a differentiation inducing material MDI (0.5 mM 3-isobutyl-1-methyl-xanthine, 1 μM dexamethasone, and 10 μg/Ml insulin), *Psoraleae* Semen, *Siegesbeckiae* Herba, and Corni Fructus extracts. The medium was removed after two days and changed into a medium containing DMEM/10% FBS, insulin, and sample. The medium was changed into a medium containing only DMEM/10% FBS, and sample after another two days. After a differentiation of 3T3-L1 preadipocytes into adipocytes was completed in a group in which a sample was introduced after a differentiation was induced, *Psoraleae* Semen, *Siegesbeckiae* Herba, and Corni Fructus extracts were treated a total three times at each concentration (1, 5, and 10 ppm) at an interval of two days.

<6-2> Protein Isolation and Quantification

In order to obtain proteins from 3T3-L1 cells, a medium was removed, the cells were twice with cold PBS (supplemented with 1 mM vanadate), RIPA lysis buffer (SC-24948) (50 mM Tris-Cl pH 7.4, 1% NP-40, 0.25% sodium deoxycholate, 0.1% SDS, 150 mM NaCl, 1 mM EDTA) was introduced at 600 μl/dish, and a shake incubation was performed at 4° C. for 10 min. After the culture was subjected to a centrifugation at 4° C. and 12,000 rpm for 20 min, only a transparent supernatant was collected, transferred to an ependorf tube, and stored at −80° C. The concentration of the protein was measured using a BCA reagent in the same manner as in HUVECs. The concentration was calculated according to the absorbance and treated with 1× Laemmli Sample Buffer at each concentration. A hot block was used to boil samples at 95° C. for 10 min and the samples were stored at −80° C.

<6-3> SDS-PAGE, Membrane Transfer and Film Phenomena

The measured protein was used to perform an electrophoresis and membrane transfer. In order to confirm the specific expression pattern of a 3T3-L1 adipocyte protein, two antibodies SREBP-1 and PPARγ, signal molecules associated with adipogenesis, were reacted at room temperature under none-fat-dry-milk (NFDM) conditions for 1 hour, diluted at a ratio of 1:1000 with 1% NFDM, and then stood still at 4° C. overnight. After the reaction was completed, the antibodies were washed four times with 1×TBST and a reaction was performed with a secondary antibody at room temperature for 1 hour. After the antibodies were washed four times with 1×TEST and a reaction was performed with a coloring agent for 5 min, a film was developed in a dark room.

Figure 15:
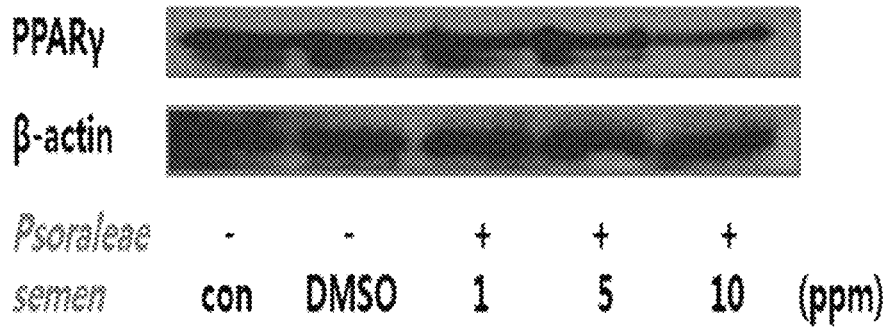
FIG. 15 is a view illustrating the inhibition of the adipocyte differentiation resulting from decrease in the expression of PPARγ by each extract of Psoraleae Semen, Siegesbeckiae Herba, and Corni Fructus of the present invention.
Figure 15:
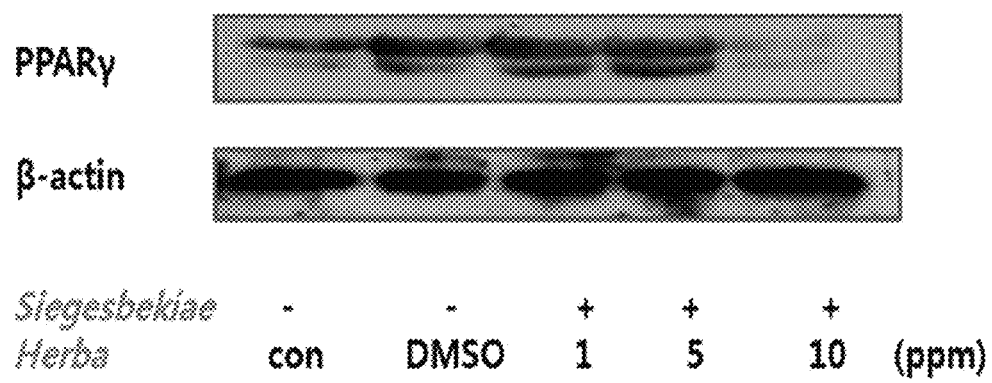
Figure 15:
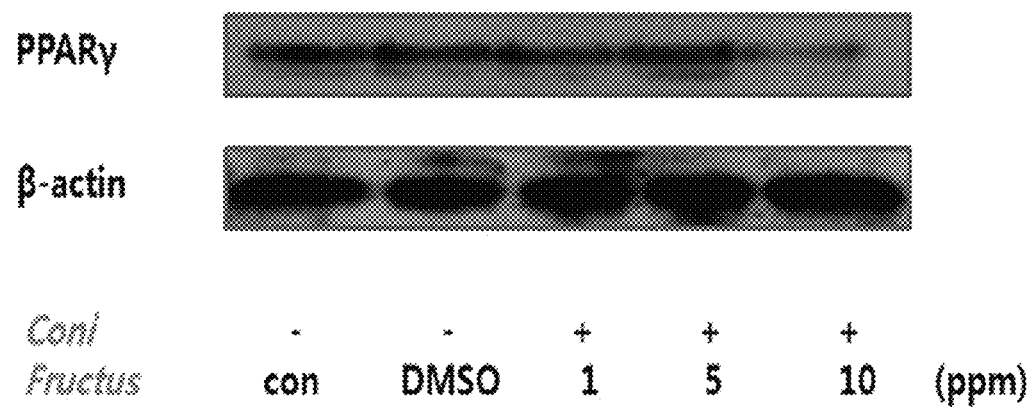

As a result, when each of *Psoraleae* Semen, *Siegesbeckiae* Herba, and Corni Fructus extracts was treated simultaneously with MDI as a differentiation inducing material, it was confirmed that the expression level of PPARγ, a signal molecule which mediates the expression of lipogenesis, decreased as the concentrations of the extracts increase as illustrated in FIG. 15. In particular, excellent lipogenesis inhibitory effects were observed at 10 ppm of *Psoraleae* Semen, *Siegesbeckiae* Herba, and Corni Fructus extracts (FIG. 15).

Figure 16:
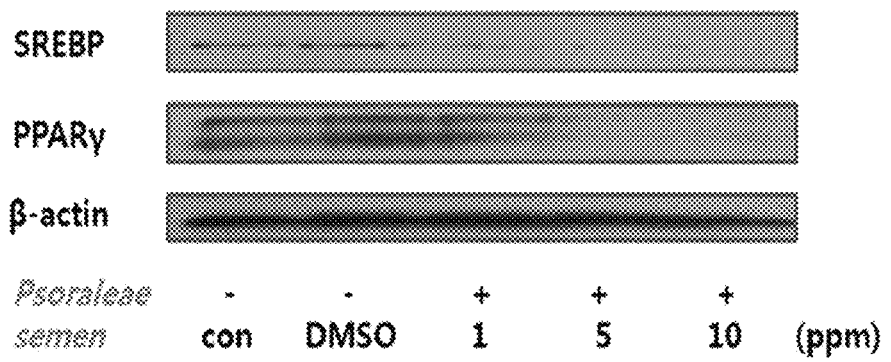
FIG. 16 is a group of photos illustrating the inhibition of the lipogenesis and adipocyte differentiation resulting from decrease in the expression of SREBP-1 and PPARγ by each extract of Psoraleae Semen, Siegesbeckiae Herba, and Corni Fructus of the present invention after a complete adipocyte differentiation.
Figure 16:
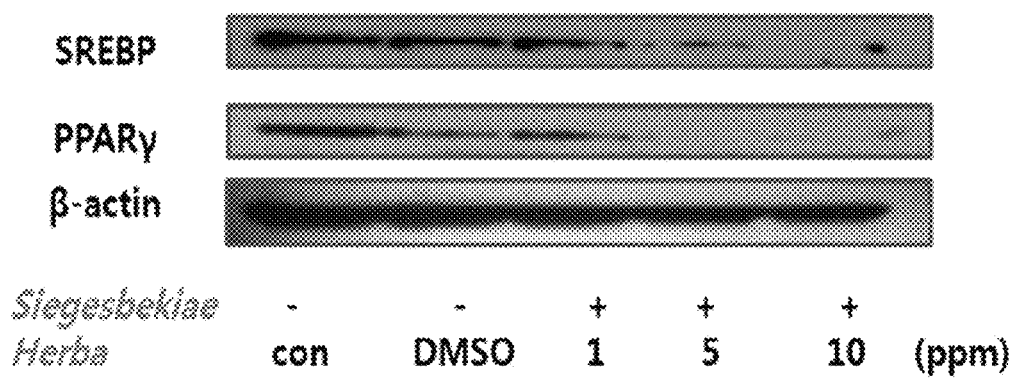
Figure 16:
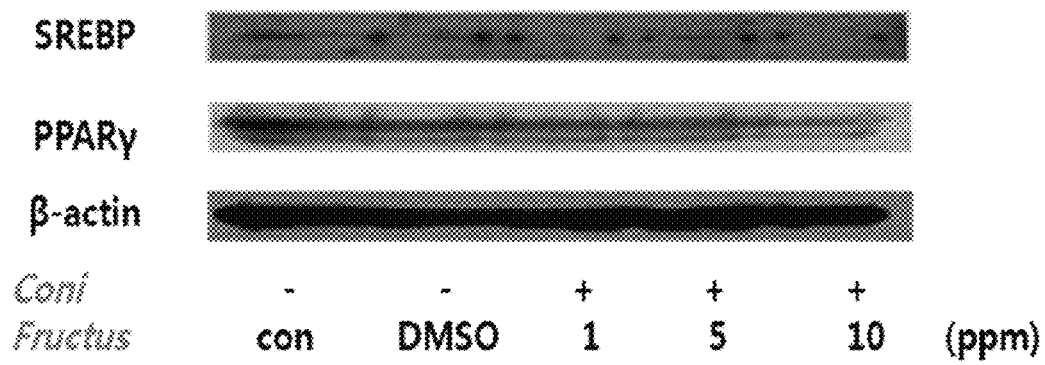

When 3T3-L1 cells were completely differentiated and then *Psoraleae* Semen, *Siegesbeckiae* Herba, and Corni Fructus extracts were treated at each concentration, it was confirmed that as illustrated in FIG. 16, the expression levels of SREBP-1 and PPARγ, signal molecules which mediate the expression of lipogenesis, decreased as the concentrations of the extracts increased (FIG. 16).

Therefore, it was confirmed that *Psoraleae* Semen, *Siegesbeckiae* Herba, and Corni Fructus extracts have lipogenesis inhibitory effects.

Experimental Example 7

Confirmation of Weight Loss Effects

<7-1> Measurement of Weight Changes

After Sprague-Dawley rats were fed a high fat diet for 16 days, 1 Ml of *Psoraleae* Semen extract at 2 mg/200 g (10 mg/kg), *Siegesbeckiae* Herba extract at 5 mg/200 g (10 mg/kg), and Corni Fructus at 5 mg/200 g (10 mg/kg) were orally administered for 15 days while they were fed a high fat diet to observe the weight changes. A control group was fed only a high fat diet without administering the extract.

Figure 17:
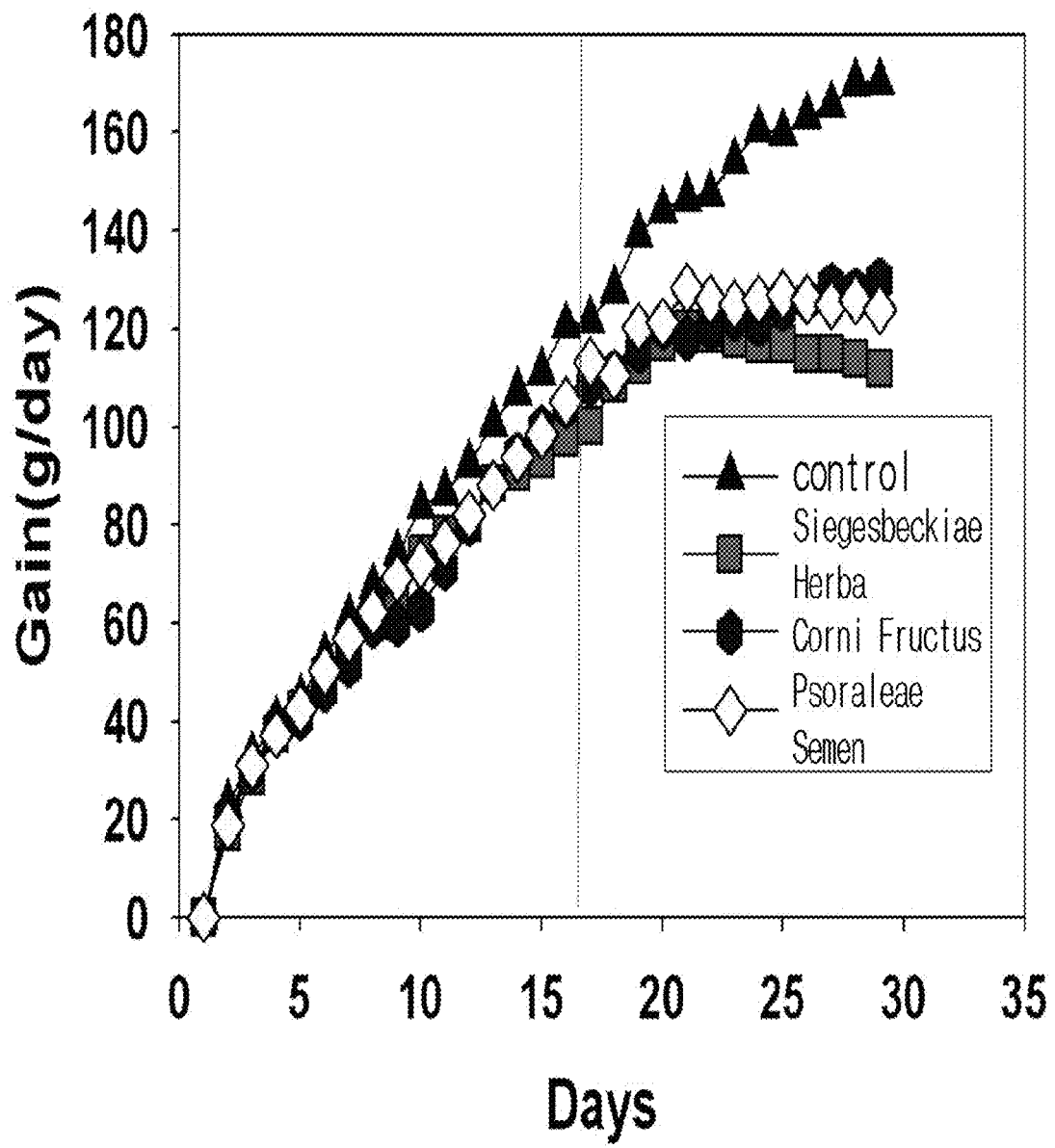
FIG. 17 is a graph illustrating the weight loss effects by each extract of Psoraleae Semen, Siegesbeckiae Herba, and Corni Fructus of the present invention.

As a result, as illustrated in FIG. 17, when a high fat diet was administered in combination with *Psoraleae* Semen, *Siegesbeckiae* Herba, and Corni Fructus extracts for 15 days, weight losses were observed by 27.1%, 34.1%, and 23.5%, respectively (FIG. 17).

<7-2> Blood Analysis

Blood was collected from the rats in <7-1> and analyzed.

As a result, as illustrated in the following Table 4, the total cholesterol levels were significantly reduced according to the administration of samples to male rats, compared to a control group. In particular, the neutral fat levels were significantly reduced except for in xenical as a positive control, and the HDL-cholesterols fell within a normal range (40 to 50 mg/dl). The total cholesterol levels in female rats were not significantly reduced compared to a control group. However, the neutral fat levels were significantly reduced compared to the level in xenical as a positive control

TABLE 4

| Sample | AST (IU/L) | ALT (IU/L) | T-CHO (mg/dl) | TG (mg/dl) | HDL-C (mg/dl) |
|---|---|---|---|---|---|
| Mcon | 524 | 98 | 174 | 124 | 28 |
| MP | 200 | 50 | 125 | 55 | 51 |
| MH | 216 | 56 | 128 | 66 | 50 |
| MS | 130 | 42 | 132 | 52 | 52 |
| MX | 116 | 38 | 116 | 150 | 50 |
| Fcon | 298 | 58 | 110 | 80 | 36 |
| FP | 154 | 44 | 106 | 58 | 36 |
| FH | 184 | 42 | 100 | 54 | 38 |
| FS | 218 | 88 | 110 | 56 | 34 |
| FX | 160 | 40 | 103 | 78 | 36 |

Mcon: male control;
MP: male pagoji (*Psoraleae semen*);
MH: male heuichum (*Siegesbekiae herba*);
MS: male sansuyu (*Corni fructus*);
MX: male xenical;
AST(U/L): GOT;
ALT(U/L): GPT;
T-CHO: Cholesterol (mg/dL): 200 mg/dl or less;
TG: Triglyceride (mg/dL): 150 mg/dl or less; and
HDL-C: HDL Cholesterol: 40-50 mg/dl or more.

Therefore, it was found that *Psoraleae* Semen, *Siegesbeckiae* Herba, and Corni Fructus induced a weight loss, accompanied by a decrease in neutral fat.

In summary, because the extracts of the present invention exhibited anti-angiogenesis effects, induced a weight loss in a short time according to the effects, and decreased the levels of the total cholesterol and neutral fat, each extract of the *Psoraleae* Semen, *Siegesbeckiae* Herba, and Corni Fructus of the present invention may be usefully used as an anti-obesity agent.

Preparation Example 1

Preparation of Pharmaceutical Formulations

1. Preparation of Powder

| | |
|---|---|
| Extract of the present invention | 2 g |
| Lactose | 1 g |

The components were mixed and filled in an airtight sac to prepare a powder agent.

2. Preparation of Tablet

| | |
|---|---|
| Extract of the present invention | 100 mg |
| Corn starch | 100 mg |
| Lactose | 100 mg |
| Magnesium stearate | 2 mg |

The components were mixed and a tableting was performed according to a conventional tablet preparation method to prepare a capsule.

3. Preparation of Capsule

| | |
|---|---|
| Extract of the present invention | 100 mg |
| Corn starch | 100 mg |
| Lactose | 100 mg |
| Magnesium stearate | 2 mg |

The components were mixed and filled into a gelatin capsule according to a conventional capsule preparation method to prepare a capsule.

4. Preparation of Pill

| | |
|---|---|
| Extract of the present invention | 1 g |
| Lactose | 1.5 g |
| Glycerin | 1 g |
| Xylitol | 0.5 g |

The components were mixed and prepared such that 4 g per pill was obtained according to a conventional method.

5. Preparation of Granule

| | |
|---|---|
| Extract of the present invention | 150 mg |
| Soybean extract | 50 mg |
| Glucose | 200 mg |
| Starch | 600 mg |

The components were mixed, 100 mg of 30% ethanol was added, and the mixture was dried at 60° C. to form a granule, which was filled in a sac.

Preparation Example 2

Preparation of Food

Foods including an extract of the present invention were prepared in the following manner.

1. Preparation of Flour Food

Food for health improvement was prepared by adding the extract of the present invention by 0.5% to 5% by weight into wheat flour, and then bread, cakes, cookies, crackers and noodles were prepared by using the mixture.

2. Preparation of Dairy Products

Various dairy products such as butter and ice cream were prepared by adding the extract of the present invention by 5% to 10% by weight into milk and using the milk.

Preparation Example 3

Preparation of Beverages

| | |
|---|---|
| Extract of the present invention | 1000 mg |
| Citric acid | 1000 mg |
| Oligosaccharide | 100 g |
| Mumefural concentrate | 2 g |
| Taurine | 1 g |
| Total by addition of purified water | 900 Ml |

According to a conventional heal beverage preparation method, the components are mixed and heated with stirring at 85° C. for about 1 hour. A resulting solution is filtered and decanted into a sterilized 2 l container with sealed and sterilized. The container is stored in a refrigerator for further use as health supplement foods of the present invention.

Although the compositions were prepared by mixing components relatively appropriate for fancy drinks in a preferred example, they may be modified considering demand class, demand country, purpose of use, local and national preference, etc.

Because the *Psoraleae* Semen extract, *Siegesbeckiae* Herba extract, and Corni Fructus extract of the present invention exhibit inhibitory effects of angiogenesis and inhibitory effects of obesity, they may be usefully used as active ingredients for a composition for prevention and treatment of angiogenesis-related diseases or obesity.

The *Psoraleae* Semen extract, *Siegesbeckiae* Herba extract, and Corni Fructus extract of the present invention may be usefully used in development of pharmaceutical composition for prevention or treatment of angiogenesis-related diseases or obesity, or of health supplement food for prevention or improvement of angiogenesis-related diseases.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating obesity, comprising administering to an individual in need thereof, a composition consisting essentially of an effective amount of a 70% ethanol extract of *Siegesbeckiae* Herba.

2. The method of claim 1, wherein the extract of *Siegesbeckiae* Herba inhibits angiogenesis.

3. The method of claim 1, wherein the composition is in a form selected from the group consisting of injectable solution, pill, capsule, granule and tablet.

4. The method of claim 1, wherein administering comprises administering about 0.01 to about 5,000 mg/kg per day to said individual.

5. The method of claim 4, wherein administering comprises administering about 0.01 to about 10 mg/kg per day to said individual.

6. The method of claim 4, wherein the composition is in a form selected from the group consisting of butter, yogurt, cheese, ice cream, bread, chocolate, candy, a confection, noodles, gum, soup, a beverage, tea, a drink, an alcoholic beverage and a vitamin complex.

7. The method of claim 4, wherein the composition further comprises a food additive selected from the group consisting of a nutrient, a vitamin, an electrolyte, a flavoring agent, a coloring agent, pectic acid or a salt thereof, an organic acid, a colloidal thickener, a pH modifier, a stabilizer, an antiseptic, glycerin, alcohol or carbonation.

8. The method of claim 4, wherein the composition is in the form of a fruit or vegetable juice.

9. The method of claim 1, wherein the composition further comprises a pharmaceutically acceptable carrier.

10. The method of claim 9, wherein the pharmaceutically acceptable carrier is selected from the group consisting of saline, sterilized water, Ringer's solution, buffered saline, dextrose solution, maltodextrose solution, glycerol, ethanol, an antioxidant, buffer solution, bacteriostatic agent, diluent, dispersing agent, surfactant, binder, lubricant and combinations thereof.

11. The method of claim 9, wherein the pharmaceutically acceptable carrier is present in the composition from about 0.0001% to about 10% by weight of the composition.

12. The method of claim 11, wherein the pharmaceutically acceptable carrier is present in the composition from 0.001% to about 1% by weight of the composition.

* * * * *